US011236400B2

(12) United States Patent
Hamilton et al.

(10) Patent No.: US 11,236,400 B2
(45) Date of Patent: Feb. 1, 2022

(54) MOLECULAR MARKERS ASSOCIATED WITH SOY IRON DEFICIENCY CHLOROSIS

(71) Applicant: SYNGENTA PARTICIPATIONS AG, Basel (CH)

(72) Inventors: Mark Charles Hamilton, Carroll, IA (US); Craig Lynn Davis, Pekin, IL (US); Jean Robert Gelin, Glyndon, MN (US); Elhan Sultan Ersoz, Johnston, IA (US); Ju-Kyung Yu, Research Triangle Park, NC (US); Thomas Joseph Curley, Research Triangle Park, NC (US); Baohong Guo, Slater, IA (US); Ainong Shi, Fayetteville, AR (US)

(73) Assignee: Syngenta Participations AG, Basel (CH)

( * ) Notice: Subject to any disclaimer, the term of this patent is extended or adjusted under 35 U.S.C. 154(b) by 75 days.

(21) Appl. No.: 16/840,815

(22) Filed: Apr. 6, 2020

(65) Prior Publication Data
US 2020/0232048 A1     Jul. 23, 2020

Related U.S. Application Data

(60) Continuation of application No. 15/843,439, filed on Dec. 15, 2017, now Pat. No. 10,648,041, which is a division of application No. 14/957,773, filed on Dec. 3, 2015, now Pat. No. 9,879,326.

(60) Provisional application No. 62/086,834, filed on Dec. 3, 2014.

(51) Int. Cl.
*A01H 5/10*     (2018.01)
*A01H 6/54*     (2018.01)
*C12Q 1/6895*     (2018.01)
*C12N 15/82*     (2006.01)

(52) U.S. Cl.
CPC ....... *C12Q 1/6895* (2013.01); *C12N 15/8271* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 7,977,533 B2 | 7/2011 | Sebastian et al. |
| 2006/0041951 A1 | 2/2006 | Sebastian et al. |
| 2011/0083234 A1* | 4/2011 | Nguyen .......... A01H 5/10 800/301 |
| 2011/0258743 A1 | 10/2011 | Sebastian et al. |
| 2014/0123346 A1 | 5/2014 | Sebastian et al. |
| 2014/0189902 A1 | 7/2014 | Chaky et al. |

OTHER PUBLICATIONS

Glycine max cDNA clone GMFL01-17-K15, NCBI/GenBank accession No. AK244954, published Nov. 19, 2008.*
Funke et al., "Physical mapping of a region in the soybean (*Glycine max*) genome containing duplicated sequences," Plant Molecular Biology, 22: 437-446, 1993.
Glycine max cDNA sequence, GenBank accession No. HO013308, published Oct. 22, 2012.

* cited by examiner

*Primary Examiner* — Bratislav Stankovic
(74) *Attorney, Agent, or Firm* — Karen A. Magri

(57) ABSTRACT

The present invention relates to methods and compositions for identifying, selecting and/or producing a soybean plant or germplasm having iron deficiency chlorosis tolerance. A soybean plant, part thereof and/or germplasm, including any progeny and/or seeds derived from a soybean plant or germplasm identified, selected and/or produced by any of the methods of the present invention is also provided.

5 Claims, No Drawings

Specification includes a Sequence Listing.

MOLECULAR MARKERS ASSOCIATED WITH SOY IRON DEFICIENCY CHLOROSIS

RELATED APPLICATION INFORMATION

This application is a continuation of U.S. application Ser. No. 15/843,439, filed 15 Dec. 2017 which is a divisional application of U.S. application Ser. No. 14/957,773, filed 3 Dec. 2015, which claims the benefit of U.S. Provisional Application No. 62/086,834, filed 3 Dec. 2014, the contents of each of which are incorporated herein by reference.

STATEMENT REGARDING ELECTRONIC FILING OF A SEQUENCE LISTING

A Sequence Listing in ASCII text format, submitted under 37 C.F.R. § 1.821, entitled 80663-US-REG-C-NAT-1 SequenceListing, 57 kilobytes in size, generated on Apr. 1, 2020 and filed via EFS-Web, is provided in lieu of a paper copy. This Sequence Listing is hereby incorporated by reference into the specification for its disclosures.

FIELD OF THE INVENTION

The present invention relates to compositions and methods for identifying, selecting and/or producing soybean plants having tolerance to iron deficiency chlorosis (IDC).

BACKGROUND

Soybean (*Glycine max* L. Merr) is a major cash crop and investment commodity in North America and elsewhere. Soybean oil is one of the most widely used edible oils, and soybeans are used worldwide both in animal feed and in human food production. Iron deficiency chlorosis (IDC) in soybeans is a widespread problem in the Upper Midwest (North Central region) of the United States and is the result of reduced availability of iron and therefore, reduced iron levels in the plant. High pH in the soil, high water tables, too much rainfall, salinity in the soil, calcium carbonate in the topsoil, and elevated soil nitrate levels all contribute to the problem. The symptoms include interveinal chlorosis (the leaves turn yellow while the veins remain green) and stunting of plant growth. If the youngest leaves and growing points are damaged due to iron deficiency, growth of the plant will be stunted and yields are reduced substantially.

Different varieties of soybean vary in their sensitivity or tolerance to iron deficiency. Therefore, one of the most effective control measures is planting IDC tolerant soybean varieties, and thus varietal selection is important for the management of IDC. However, currently, determining whether a soybean cultivar might have tolerance to IDC typically involves testing each cultivar in the field or greenhouse under conditions that typically produce IDC. Thus, the present invention overcomes the shortcomings in the art by providing markers associated with tolerance to IDC, thereby allowing the characterization of soybean cultivars for IDC tolerance by molecular analysis rather than phenotypic analysis.

SUMMARY OF THE INVENTION

Compositions and methods for identifying, selecting and/or producing soybean plants with tolerance to iron deficiency chlorosis (IDC) are provided. As described herein, a marker associated with enhanced IDC tolerance may comprise, consist essentially of or consist of a single allele or a combination of alleles at one or more genetic loci.

Accordingly, in one aspect of the present invention, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein said marker is located within a chromosomal interval on chromosome 5 defined by and including a T allele at IIY12124, a G allele at IIY12130, a A allele at IIY12132 SEQ ID NO 3 or any combination thereof; (b) a chromosomal interval on chromosome 7 defined by and including a A allele at IIY13279, a G allele at SY0106A, a G allele at SY0642A, or any combination thereof; (c) a chromosomal interval on chromosome 13 defined by and including a C allele at SY0132A, a A allele at SY1091 A, or any combination thereof; and (k) any combination of (a) through (c) and selecting a progeny soybean plant or germplasm that possesses said marker within its genome, thereby selecting an IDC tolerant soybean plant or germplasm.

In another aspect, the present invention provides a method of identifying and/or selecting an iron deficiency chlorosis (IDC) tolerant soybean plant or part thereof, comprising: detecting, in said soybean plant or part thereof, the presence of a marker associated with IDC tolerance, wherein said marker is selected from the group consisting of: (a) a A allele at IIY712; (b) a A allele at SY0622A; (c) a G allele at SY0023A; (d) an T allele at IIY9605; (e) a T allele at IIY12124; (f) a G allele at IIY12132; (g) a G allele at IIY12130; (h) a A allele at IIY13279; (i) a G allele at SY0106A; (j) a G allele at SY0642A; (k) a C allele at SY0132A; (l) a A allele at SY1091A; (m) a A allele at IIY16255; (n) a A allele at IIY6614; (o) a A allele at IIY6608; (p) a G allele at IIY6613; and any combination of (a) through (p) above, thereby identifying and/or selecting an IDC tolerant soybean plant or part thereof.

In an additional aspect of the present invention, a method of identifying and/or selecting an iron deficiency chlorosis (IDC) tolerant soybean plant or part thereof is provided, the method comprising: detecting, in said soybean plant or part thereof, the presence of a combination of genetic markers (haplotype) associated with IDC tolerance in a soybean plant, the combination of genetic markers selected from the group consisting of: (a) a A allele at IIY712; (b) a A allele at SY0622A; (c) a G allele at SY0023A; (d) an T allele at IIY9605; (e) a T allele at IIY12124; (f) a G allele at IIY12132; (g) a G allele at IIY12130; (h) a A allele at IIY13279; (i) a G allele at SY0106A; (j) a G allele at SY0642A; (k) a C allele at SY0132A; (l) a A allele at SY1091A; (m) a A allele at IIY16255; (n) a A allele at IIY6614; (o) a A allele at IIY6608; (p) a G allele at IIY6613; and any combination of (a) through (p) above, thereby identifying and/or selecting an IDC tolerant soybean plant or part thereof.

In other aspects, the present invention provides a method of producing an iron deficiency chlorosis (IDC) tolerant soybean plant or part thereof, comprising: detecting, in a soybean germplasm, the presence of a marker associated with IDC tolerance in a soybean plant, wherein said marker is located within a chromosomal interval selected from the group consisting of: (a) a chromosomal interval on chromosome 5 defined by and including a T allele at IIY12124, a G allele at IIY12130, a A allele at IIY12132 or any combination thereof; (b) a chromosomal interval on chromosome 7 defined by and including a A allele at IIY13279, a G allele at SY0106A, a G allele at SY0642A, or any combination thereof; (c) a chromosomal interval on chromosome 13 defined by and including a C allele at SY0132A, a A allele at SY1091A, or any combination thereof; and (k) any combination of (a) through (c) above, and producing a soybean plant from said soybean germplasm, thereby producing an IDC tolerant soybean plant or part thereof.

In further aspects of the invention, a method of producing an iron deficiency chlorosis (IDC) tolerant soybean plant or part thereof is provided, the method comprising: detecting, in a soybean germplasm, the presence of a marker associated with IDC tolerance, wherein said marker is selected from the group consisting of: (a) a A allele at IIY712; (b) a A allele at SY0622A; (c) a G allele at SY0023A; (d) an T allele at IIY9605; (e) a T allele at IIY12124; (t) a G allele at IIY12132; (g) a G allele at IIY12130: (h) a A allele at IIY13279; (i) a G allele at SY0106A; (j) a G allele at SY0642A; (k) a C allele at SY0132A; (1) a A allele at SY1091A; (m) a A allele at IIY16255; (n) a A allele at IIY6614; (o) a A allele at IIY6608; (p) a G allele at IIY6613; and any combination of (a) through (p) above, thereby identifying and/or selecting an IDC tolerant soybean plant or part thereof.

In additional aspects, a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a marker associated with IDC tolerance in a soybean plant, wherein said marker is located within a chromosomal interval selected from the group consisting of (a) a chromosomal interval on chromosome 5 defined by and including a T allele at IIY12124, a G allele at IIY12130, a A allele at IIY12132 or any combination thereof; (b) a chromosomal interval on chromosome 7 defined by and including a A allele at IIY13279, a G allele at SY0106A, a G allele at SY0642A, or any combination thereof; (c) a chromosomal interval on chromosome 13 defined by and including a C allele at SY0132A, a A allele at SY1091A, or any combination thereof; and (k) any combination of (a) through (c) and selecting a progeny soybean plant or germplasm that possesses said marker within its genome, thereby selecting an IDC tolerant soybean plant or germplasm.

Other aspects of the present invention provide a method of selecting an iron deficiency chlorosis (IDC) tolerant soybean plant or germplasm, comprising: crossing a first soybean plant or germplasm with a second soybean plant or germplasm, wherein said first soybean plant or germplasm comprises within its genome a marker associated with IDC tolerance in a soybean plant, wherein said marker is selected from the group consisting of: (a) a A allele at IIY712: (b) a A allele at SY0622A; (c) a G allele at SY0023A; (d) an T allele at IIY9605; (e) a T allele at IIY12124; (f) a G allele at IIY12132; (g) a G allele at IIY12130; (h) a A allele at IIY13279; (i) a G allele at SY0106A; (j) a G allele at SY0642A; (k) a C allele at SY0132A; (1) a A allele at SY1091A; (m) a A allele at IIY16255; (n) a A allele at IIY6614; (o) a A allele at IIY6608; (p) a G allele at IIY6613: and any combination of (a) through (p) above, thereby identifying and/or selecting an IDC tolerant soybean plant or part thereof.

In other embodiments, the present invention provides a method of selecting an iron deficiency chlorosis (IDC) tolerant soybean plant or germplasm is provided, the method comprising: crossing a first soybean plant or germplasm with a second soybean plant or germplasm, wherein said first soybean plant or germplasm comprises within its genome a combination of genetic markers (haplotype) associated with IDC tolerance in a soybean plant, the combination of genetic markers selected from the group consisting of: (a) a A allele at IIY712; (b) a A allele at SY0622A; (c) a G allele at SY0023A; (d) an T allele at IIY9605; (e) a T allele at IIY12124; (f) a G allele at IIY12132; (g) a G allele at IIY2130; (h) a A allele at IIY13279 (i) a G allele at SY0106A; (j) a G allele at SY0642A; (k) a C allele at SY0132A; (1) a A allele at SY1091A; (m) a A allele at IIY16255; (n) a A allele at IIY6614; (o) a A allele at IIY6608; (p) a G allele at IIY6613; and any combination of (a) through (p) above; and selecting a progeny soybean plant or germplasm that possesses said marker within its genome, thereby selecting an IDC tolerant soybean plant or germplasm.

Another aspect of the invention is that some markers have been surprisingly associated with IDC tolerance in both soil type 1 and soil type 2. Soil type 1 includes U.S. soils found Southern Minnesota and Northern Iowa often referred to as glacial deposits. Soil Type 2 refers to soil found in the U.S. Red River Valley area that includes most of North Dakota and Northern Minnesota often referred to as lake bed over glacial deposits. The following markers have been identified to work in a wider geographical area including both soil types 1 and 2 comprising (a) a A allele at IIY712; (b) a A allele at SY0622A; (c) a G allele at SY0023A; (d) an T allele at IIY9605; (e) a T allele at IIY12124; (f) a G allele at IIY12132: (g) a G allele at IIY12130; (h) a A allele at IIY13279; (i) a G allele at SY0106A; (j) a G allele at SY0642A, (k) a G allele at SY0781AQ, (1) a G allele at SY0152AQ, (m) a G allele at SY1069AQ, (n) a G allele at SY2140AQ, (o) a A allele at SY0632AQ and any combination of (a) through (o) above, thereby identifying and/or selecting an IDC tolerant soybean plant or part to be grown in either soil type 1, soil type 2 or both.

Another aspect of the invention provides for markers and/or genes within a soybean chromosomal interval that associate with IDC tolerance wherein said soybean chromosomal interval is: on soybean chromosome 2 wherein the interval is defined by at least two of SY0781AQ, SY0322AQ, or SY1300AQ; on soybean chromosome 3 wherein the interval is defined by at least two of SY0673AQ and SY0674AQ; on soybean chromosome 5 wherein the interval is defined by at least two of SY3925, IIY12130, IIY12132, or SY0152AQ: on soybean chromosome 7 wherein the interval is defined by at least two of SY0106A, SY0642A, or IIY13279; on soybean chromosome 9 wherein the interval is defined by at least two of IIY712 and SY1069AQ; on soybean chromosome 13 wherein the interval is defined by at least two of SY3929, SY1258AQ, SY1091A, SY0132A, SY0023A, or SY3931; on soybean chromosome 14 wherein the interval is defined by at least two of SY0121AQ and SY0224AQ; on soybean chromosome 15 wherein the interval is defined by at least two of SY0386AQ, SY0952AQ or SY0808AQ; on soybean chromosome 16 wherein the interval is defined by at least two of IIY6608, IIY16255, IIY6613, or IIY6614; on soybean chromosome 19 wherein the interval is defined by at least two of SY0622A, SY0066AQ, or SY0632AQ.

Another aspect of the invention provides for methods of identifying, selecting or producing IDC tolerant soybean plants through the use of markers as shown in Table 1. Further the invention provides for methods of introducing IDC tolerant soybean plants wherein introducing encompasses introgression of chromosome interval comprising a marker and/or gene that confers IDC tolerance into a plant. Additionally, introducing can mean the use of gene editing tools (e.g. TALEN, CRISPR, etc.) to create allelic variants having favorable genotypes as described herein (e.g. as shown in Table 1). The term introducing can mean the introduction of genes within close proximity of the markers listed in Table 1 wherein close proximity can be for example 10 cM, 5 cM, 2 cM, 1 cM, 10000 nucleotide base-pairs (bp), 5000 bp, 2500 (bp), 1000 (bp), 500 bp or 250 bp within the physical position of a marker described in Table 1. Finally, the term introducing can mean the heterologous expression of a gene in close proximity to any marker in Table 1 in a plant to create a IDC tolerant plant.

Soybean plants and/or germplasms identified, produced or selected by the methods of this invention are also provided, as are any progeny and/or seeds derived from a soybean plant or germplasm identified, produced or selected by these methods.

These and other aspects of the invention are set forth in more detail in the description of the invention below.

DETAILED DESCRIPTION

The present invention provides compositions and methods for identifying, selecting and/or producing soybean plants having iron deficiency tolerance, as well as soybean plants and parts thereof, including but not limited to seeds, that are identified, selected and/or produced by a method of this invention. The present invention further provides an assay for the detection of IDC in a soybean plant. In addition, the present invention provides soybean plants and/or soybean germplasm having within their genomes one or more SNP or QTL markers associated with tolerance to iron deficiency chlorosis.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications and sequences referenced herein are incorporated by reference in their entireties.

Definitions

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker (e.g., SNP, QTL, haplotype) can mean one marker or a plurality of markers (e.g., 2, 3, 4, 5, 6, and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with tolerance to iron deficiency chlorosis in a soybean plant relative to a control soybean plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with an IDC tolerance allele" refers to a marker whose presence or absence can be used to predict whether a plant will display tolerance to iron deficiency chlorosis.

Iron deficiency chlorosis (IDC) is a physiological disease in soybean plants that is caused by a lack of iron in the plant. Most soils contain sufficient iron. However, in some soils the iron is insoluble and thus unavailable to the plants. As a result of the unavailability of the iron in the soil, plants grown in such soil lack iron. It is also known in the art that IDC can be the result of any one or combination of a) the plant's inability to uptake iron from the soil (e.g. iron insolubility, or root uptake hindered), b) the inability of the plant to transport the iron to the leaf and c) the inability of the plant to activate the iron in the leaf. Any one of these (a-c) scenarios can lead to the symptoms that are indicative of IDC. Herein, the terms "Iron deficiency chlorosis" or "IDC" interchangeably represent a physiological disease in any plant that is caused by the lack of iron whether that lack of iron is due to the plant's inability to uptake the iron; a plant's inability to transport the iron or thirdly the plant's inability to activate the iron in the leaf tissue.

As used herein, the terms "low iron," "low iron conditions," "low iron growth conditions," "low iron availability" or "iron deficiency" or the like refer to conditions where iron availability is less than optimal for soybean growth and can cause physiological disease, e.g., iron deficiency chlorosis, due to the lack of soluble or available iron in the growth medium (e.g., soil). While the absolute level of iron may be sufficient, the form of the iron, which is affected by various environmental factors, may make the iron that is present unavailable for plant use (cannot be taken up by the plant's roots). See. Dahiya and Singh. *Plant and Soil* 51:13-18 (1979). For example, high carbonate levels, high pH, high salt content (high salinity; e.g., phosphorus, manganese and zinc), saturated soils (and/or poor drainage) and/or other environmental factors can result in lower iron solubility; thereby, reducing the solubilized forms of iron that are necessary for plant uptake. Thus, soils having low available iron include, but are not limited to, those that are calcareous (i.e., high in calcium carbonate) and have a high pH (greater than 7.5). Iron levels in soil that are optimal/not optimal for plant growth are well known in the art as are methods for measuring iron content.

The initial symptoms of iron deficiency chlorosis include interveinal chlorosis in the newly developing trifoliate leaves. Interveinal chlorosis can be described as a contrast of the inter-vein tissue color, which turns yellow, as compared to the vein color, which remains green. The interveinal chlorosis is referred to as "yellow flash." Yellow flash occurs at about 21 days after planting or at the V2 stage of growth. Eventually, the leaves of symptomatic plants may develop necrotic spots that coalesce and then, finally the leaves may fall off. Tolerant varieties may express more normal leaf color and little contrast between inter-vein tissue color and vein color. Intolerant varieties express greenish-yellow or yellow or yellowish-white colored inter-vein tissue while the vein remains green which produces relatively greater and greater contrast. Intolerant varieties are also slow in vegetative growth and biomass compared to tolerant varieties. Extremely intolerant varieties produce white trifoliate leaves that quickly decline and become necrotic. Extremely intolerant plants essentially stop growing vegetatively, producing maximum contrast compared to tolerant varieties.

The term "recovery" as used herein refers to the extent of iron deficiency chlorosis symptoms as measured in newly developed leaves or about 14 days after the initial yellow flash. Tolerant varieties signal recovery by producing a more normal green color in the new leaves (i.e., little contrast between leaf tissue and veinal tissue) as compared to the initial yellow flash response measured earlier in that same plant. Intolerant varieties continue to produce yellow flash symptoms in the new leaves resulting in a continuing contrast between interveinal tissue and the veins, as discussed herein.

As used herein, the term "iron deficiency tolerance" or "iron deficiency chlorosis tolerance" refers to a plant's ability to have increased efficiency in uptake of, transporting and activating iron as compared to one or more control plants not tolerant to IDC (e.g., a plant lacking a marker associated with iron deficiency tolerance). In some cases an iron deficiency tolerant plant can uptake iron, transport iron or activate iron once in the leaf tissue at an increased or more efficient rate than a control plant not tolerant to iron deficiency chlorosis grown in the same or similar environment Thus, "tolerance" in a soybean plant to iron deficient or low iron growth conditions is an indication that the soybean plant is less affected by the low iron growth conditions with respect to yield, survivability and/or other relevant agronomic measures, compared to a less tolerant, more "susceptible" plant. Tolerance is a relative term, indicating that a "tolerant" soybean plant survives and/or produces a better yield in iron deficient growth conditions when compared to a different (less tolerant) soybean plant (e.g., a different soybean strain or variety) grown in similar conditions of low iron availability. That is, under iron deficient growth conditions a tolerant plant can have a greater survival rate and/or yield, as compared to a soybean plant that is susceptible or intolerant to these low iron growth conditions. Iron deficiency "tolerance" sometimes can be used interchangeably with iron deficiency "resistance." Iron deficiency chlorosis intolerant soybean varieties and cultivars are well known in the art. A non-limiting example of an IDC intolerant soybean cultivar is soybean cultivar M08851 (U.S. Pat. No. 7,126, 047).

In some embodiments, a plant of this invention that is iron deficiency tolerant or iron deficiency chlorosis tolerant includes a plant that exhibits reduced yellow flash symptoms as compared to a plant not having in its genome the genetic markers described herein as associated with IDC tolerance. In other embodiments, a plant of this invention that is IDC tolerant also includes a plant that exhibits recovery from yellow flash as compared to a plant not having in its genome the genetic markers described herein as associated with IDC tolerance. In still other embodiments, a plant of this invention that is iron deficiency tolerant includes a plant that exhibits both reduced yellow flash symptoms and recovery from yellow flash as compared to a plant not having in its genome the marker(s) described herein as associated with IDC tolerance.

As is understood by the skilled artisan, soybean plant tolerance to low-available iron conditions varies widely, and can represent a range of more tolerant to less-tolerant phenotypes. Non-limiting examples of methods for determining the relative tolerance or susceptibility of different plants, plant lines or plant families under low-available iron conditions include visual observation (e.g., visual chlorosis scoring system) (See, Helms et al. Agronomy J 102:492-498 (2010)) and/or electronic scanning using a Greenseeker® RT100 radiometer (See, PCT/US10/46303; WO/2011/ 022719). Other methods for determining IDC tolerance include but are not limited to the use of hydroponics (See, Niebur and Fehr. *Crop Sci.* 21:551-554 (1981)).

In the case of a visual chlorosis scoring system, a plant that is grown in soil having low available iron, or in low available iron experimental conditions, can be assigned a tolerance rating of between 1 (highly tolerant; yield and survivability not significantly affected; all plants normal green color) to 9 (highly susceptible; most or all plants dead; those that live are stunted and have little living tissue) based on visual observation of the level of chlorosis in the plant.

In a further example, a radiometer can be used to take electronic measurements. In this case, a plant that is grown in a known low available iron soil, or in low available iron experimental conditions, is assigned a tolerance rating of between 1 (highly tolerant; yield and survivability not significantly affected; all plants normal green color) to 0 (highly susceptible; most or all plants dead; those that live are stunted and have little living tissue) based on the reading provided by scanning the foliage with the radiometer.

As used herein, the terms "backcross" and "backcrossing" refer to the process whereby a progeny plant is crossed back to one of its parents one or more Limes (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent. "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with IDC tolerance may be introgressed from a donor into a recurrent parent that is IDC intolerant. The resulting offspring could then be backcrossed one or more times and selected until the progeny possess the genetic marker(s) associated with iron deficiency chlorosis tolerance in the recurrent parent background.

As used herein, the term "linkage" refers to the degree with which one marker locus is associated with another marker locus or some other locus (for example, an IDC tolerance locus). The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., IDC tolerance. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234: 177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase internet resource (soybase.org). In some embodiments, a genetic marker of this invention is an SNP allele, a SNP allele located in a chromosome interval and/or a haplotype (combination of SNP alleles) each of which is associated with IDC tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Table 2)

Accordingly, in some embodiments of this invention, a marker is detected by amplifying a *Glycine* sp. nucleic acid with two oligonucleotide primers by, for example, the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Non-limiting examples of probes of this invention include SEQ ID NOs: 19-54 and 137-300.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition.* Cold Spring Harbor Laboratory Press, Cold Spring Harbor, N.Y., United States of America. Generally, lower salt concentration and higher temperature hybridization and/or washes increase the stringency of hybridization conditions.

As used herein, the term "probe" refers to a single-stranded oligonucleotide sequence that will form a hydrogen-bonded duplex with a complementary sequence in a target nucleic acid sequence analyte or its cDNA derivative.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP. BestFit. PlotSimilarity. and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk. A. M., ed.) Oxford University Press, New York (1988); *Biocomputing: Informatics and Genome Proj-* ects (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov. M. and Devereux. J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST®X version 2.0 for translated nucleotide sequences and BLAST®N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman. *Adv. Appl. Math.,* 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST@) programs which are publicly available from National Center Biotechnology Information (NCBI) at the National Library of Medicine, National Institute of Health, Bethesda. Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence BLAST®X can be used to determine sequence identity; and for polynucleotide sequence BLAST®N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "soybean" refers to a plant, and any part thereof, of the genus *Glycine* including, but not limited to *Glycine max*.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny", "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

As used herein, the term "reference sequence" refers to a defined nucleotide sequence used as a basis for nucleotide sequence comparison (e.g., Chromosome 3 of *Glycine max* cultivar Williams 82). The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

Genetic Mapping

Genetic loci correlating with particular phenotypes, such as tolerance to iron deficiency chlorosis, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with tolerance to iron deficiency chlorosis in soybean. Detection of these markers and/or other linked markers can be used to identify, select and/or produce soybean plants having IDC tolerance and/or to eliminate soybean plants from breeding programs or from planting that do not have IDC tolerance Markers Associated with Tolerance to Iron Deficiency Chlorosis Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP. STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) Methods in Plant Molecular Biology and Biotechnology, CRC Press, Boca Raton, Fla., United States of America; Zietkiewicz et al. (1994) Genomics 20:176-183.

Table 1 provides a summary of markers associated with IDC tolerance in soybean, their corresponding name, the physical location of the marker on the respective soybean chromosome, and the target allele that is associated with IDC tolerance.

Markers of the present invention are described herein with respect to the positions of marker loci in the 8X public build of the Williams82 soybean genome at the SoyBase internet resource (soybase.org/SequenceIntro.php) or USDA at (bfgl.anri.barc.usda.gov/cgi-bin/soybean/Linkage.pl). See Table 1 below.

TABLE 1

Summary of genetic regions associated with IDC.

| Assay Name | Soybean Chromosome | Physical Position in Williams82 Genome | Traits | SEQ ID NO for DNA fragment comprising SNP (SNP position) | SEQ ID NOs for exemplary Primer/Probe sequences | Favorable Allele/ Unfavorable Allele |
|---|---|---|---|---|---|---|
| SY0781AQ | 2 | 2850183 | IC_N | 1(255) | 36-37/38-39 | G/A |
| SY0322AQ | 2 | 3091839 | IC_N | 2(330) | 40-41/42/43 | T/A |
| SY1300AQ | 2 | 4189924 | IC_N | 3(61) | 44-45/46-47 | C/A |
| SY0673AQ | 3 | 45098253 | ICFLR; IC_N | 4(424) | 48-49/50-51 | A/C |
| SY0674AQ | 3 | 45416367 | ICFLR; IC_N | 5(229) | 52-53/54-55 | A/G |
| SY3925 | 5 | 8817107 | YVA (ICFAR) | 6(201) | 56-57/58-59 | T/A |
| IIY12130 | 5 | 8937527 | YVA (ICFAR) | 7(201) | 60 | G/A |
| IIY12132 | 5 | 8965937 | YVA (ICFAR) | 8(201) | 61 | G/A |
| SY0152AQ | 5 | 1035989 | IC_R; IC_N | 9(125) | 62-63/64-65 | G/A |
| SY0106A | 7 | 5227284 | YVA (ICFAR) | 10(191) | 66-67/68-69 | G/C |
| SY0642A | 7 | 5227284 | YVA (ICFAR) | 11(191) | 70-71/72-73 | G/C |
| IIY13279 | 7 | 7735885 | YVA (ICFAR) | 12(201) | 74-75 | A/T |
| IIY712 | 9 | 38965186 | YVA (ICFAR) | 13(434) | 76-77 | A/T |
| SY1069AQ | 9 | 40300598 | YVA (ICFAR) | 14(117) | 78-79/80-81 | G/A |
| SY2140AQ | 10 | 44378814 | ICFLR; IC_N | 15(251) | 82-83/84-85 | G/A |
| SY0498AQ | 12 | 36574820 | IC_N | 16(477) | 86-87/88-89 | G/A |
| SY3929 | 13 | 28861276 | ICFLR; IC_N | 17(501) | 90-91/92-93 | G/A |
| SY1258AQ | 13 | 29310338 | ICFLR; IC_N | 18(327) | 94-95/96-97 | G/A |
| SY1091A | 13 | 29702280 | YVA (ICFAR) | 19(90) | 98-99/100-101 | A/G |
| SY0132A | 13 | 29825027 | YVA (ICFAR) | 20(131) | 102-103/104-105 | C/A |
| SY0023A | 13 | 30771524 | YVA (ICFAR) | 21(381) | 106-107/108-109 | G/A |
| SY3931 | 13 | 31004768 | ICFAR | 22(501) | 110-111/112-113 | A/T |
| SY0121AQ | 14 | 1359785 | ICFLR; IC_N | 23(619) | 114-115/116-117 | A/C |
| SY0224AQ | 14 | 4305821 | ICFLR; IC_N | 24(187) | 118-119/120-121 | A/T |
| SY0386AQ | 15 | 5897794 | IC_R; IC_N | 25(465) | 122-123/124-125 | A/G |
| SY0952AQ | 15 | 7030013 | YVA (ICFAR) | 26(311) | 126-127/128-129 | G/A |
| SY0808AQ | 15 | 32474587 | ICFLR | 27(292) | 130-131/132-133 | G/A |

TABLE 1-continued

Summary of genetic regions associated with IDC.

| Assay Name | Soybean Chromosome | Physical Position in Williams82 Genome | Traits | SEQ ID NO for DNA fragment comprising SNP (SNP position) | SEQ ID NOs for exemplary Primer/Probe sequences | Favorable Allele/ Unfavorable Allele |
|---|---|---|---|---|---|---|
| IIY6608 | 16 | 7372457 | YVA (ICFAR) | 28(201) | 134 | A/G |
| IIY16255 | 16 | 7421364 | YVA (ICFAR) | 29(251) | 135 | A/G |
| IIY6613 | 16 | 7421475 | YVA (ICFAR) | 30(201) | 136 | G/A |
| IIY6614 | 16 | 7441547 | YVA (ICFAR) | 31(201) | 137-138 | A/T |
| SY0622A | 19 | 40201168 | YVA (ICFAR; ICRAR; ICFAN RVA; ICRAN) | 32(434) | 139-140/141-142 | A/C |
| SY0066AQ | 19 | 40773864 | ICFAN | 33(568) | 143-144/145-146 | G/A |
| SY0632AQ | 19 | 48091800 | ICFLR; IC_N ICFAR; ICRAR; ICRAN; | 34(81) | 147-148/149-150 | A/G |
| IIY9605 | 20 | 35291114 | ICRAN | 35(201) | 151-152 | T/A |

Table 2 provides a summary of marker positions that are statistically associated with IDC tolerance. Markers from Table 2 may be used to select, identify or produce soybean plants that are IDC tolerant.

TABLE 2

Summary of marker positions that statistically associate with IDC tolerance in soybean. Chromosome physical position points correspond with Williams 82 reference sequence (i.e. 8X public build of the Williams82 soybean genome at the SoyBase internet resource (soybase.org/SequenceIntro.php) or USDA at (bfgl.anri.barc.usda.gov/cgi-bin/soybean/Linkage.pl).

| Marker Name | Chromosome # | Physical Position |
|---|---|---|
| IIY1731 | 1 | 2696842 |
| IIY1794 | 1 | 3361120 |
| IIY1987 | 1 | 48174959 |
| IIY1840 | 1 | 39251460 |
| IIY1846 | 1 | 39598517 |
| IIY17813 | 1 | 41992944 |
| IGGY2483 | 1 | 39249687 |
| IIY17388 | 1 | 44787967 |
| IIY1935 | 1 | 44365728 |
| IIY17427 | 1 | 38704520 |
| IIY17110 | 1 | 43075379 |
| IGGY2445 | 1 | 43025867 |
| IIY2007 | 1 | 48469424 |
| IIY381 | 1 | 45165995 |
| IIY8883 | 2 | 3571878 |
| IIY17463 | 2 | 3535661 |
| IIY268 | 2 | 2381400 |
| IIY17262 | 2 | 3334278 |
| IIY201 | 2 | 2144787 |
| IIY8885 | 2 | 3574125 |
| IIY8900 | 2 | 3798059 |
| IIY8907 | 2 | 3826932 |
| IIY8930 | 2 | 4130147 |
| IIY17269 | 2 | 4152757 |
| IIY8953 | 2 | 4225831 |
| IIY15005 | 2 | 4333374 |
| IIY18 | 2 | 4344854 |
| IIY19423 | 5 | 464085 |
| IIY12065 | 5 | 528958 |
| IIY12107 | 5 | 8590432 |
| IIY14727 | 5 | 8680438 |
| IGGY2242 | 5 | 8680438 |
| IIY12119 | 5 | 8690578 |
| IIY19434 | 5 | 8711271 |
| IIY12122 | 5 | 8793760 |
| IIY12124 | 5 | 8817107 |
| IIY12132 | 5 | 8965937 |
| IIY714 | 5 | 9097414 |
| IGGY2577 | 5 | 24873202 |

TABLE 2-continued

Summary of marker positions that statistically associate with IDC tolerance in soybean. Chromosome physical position points correspond with Williams 82 reference sequence (i.e. 8X public build of the Williams82 soybean genome at the SoyBase internet resource (soybase.org/SequenceIntro.php) or USDA at (bfgl.anri.barc.usda.gov/cgi-bin/soybean/Linkage.pl).

| Marker Name | Chromosome # | Physical Position |
|---|---|---|
| IIY12773 | 6 | 9187422 |
| IIY1159 | 6 | 9621882 |
| IIY14865 | 6 | 10054383 |
| IIY12149 | 6 | 10122552 |
| IIY1217 | 7 | 4835105 |
| IIY17933 | 7 | 5014857 |
| IIY1219 | 7 | 5150928 |
| IIY13170 | 7 | 5158922 |
| IGGY3022 | 7 | 5227284 |
| IIY13183 | 7 | 5366035 |
| IIY13185 | 7 | 5484851 |
| IIY13189 | 7 | 5603441 |
| IIY13191 | 7 | 5636973 |
| IIY13197 | 7 | 5902793 |
| IIY13206 | 7 | 5964630 |
| IIY13209 | 7 | 5983847 |
| IIY13221 | 7 | 6370540 |
| IGGY821 | 7 | 6404645 |
| IGGY1808 | 7 | 6404690 |
| IIY13248 | 7 | 6775437 |
| IIY1221 | 7 | 6850608 |
| IIY13279 | 7 | 7735885 |
| IIY13284 | 7 | 7807344 |
| IIY1226 | 7 | 7813163 |
| IIY18900 | 7 | 8346282 |
| IIY328 | 7 | 8426971 |
| IIY15798 | 7 | 8427812 |
| IIY13323 | 7 | 8481040 |
| IIY13334 | 7 | 8596256 |
| IIY13340 | 7 | 8683036 |
| IIY1260 | 8 | 12458183 |
| IIY807 | 8 | 12971581 |
| IIY13425 | 8 | 13896731 |
| IIY1286 | 9 | 3110521 |
| IIY14156 | 9 | 3399524 |
| IIY625 | 9 | 3447521 |
| IIY18960 | 9 | 3822389 |
| IIY14596 | 9 | 5464507 |
| HY18894 | 9 | 5568002 |
| IIY14600 | 9 | 5569484 |
| IIY20441 | 12 | 7941435 |
| IIY20488 | 12 | 8011912 |
| IIY3994 | 12 | 9772990 |
| IIY600 | 12 | 10342367 |
| IIY3377 | 12 | 10990890 |

TABLE 2-continued

Summary of marker positions that statistically associate with IDC tolerance in soybean. Chromosome physical position points correspond with Williams 82 reference sequence (i.e. 8X public build of the Williams82 soybean genome at the SoyBase internet resource (soybase.org/SequenceIntro.php) or USDA at (bfgl.anri.barc.usda.gov/cgi-bin/soybean/Linkage.pl).

| Marker Name | Chromosome # | Physical Position |
|---|---|---|
| IIY20714 | 12 | 11193280 |
| IGGY2960 | 12 | 13635572 |
| IIY4052 | 13 | 13666288 |
| IIY4055 | 13 | 14552235 |
| IIY4064 | 13 | 17544665 |
| IIY4069 | 13 | 20039573 |
| IIY141 | 13 | 20365685 |
| IIY4072 | 13 | 20419690 |
| IIY4073 | 13 | 20423675 |
| IIY20140 | 13 | 20805842 |
| IIY20141 | 13 | 20828611 |
| IIY21977 | 13 | 20989581 |
| IIY20302 | 13 | 21511291 |
| IIY20413 | 13 | 23107929 |
| IIY116 | 13 | 23209914 |
| IIY20038 | 14 | 2269239 |
| IIY4907 | 14 | 2322359 |
| IIY4908 | 14 | 2329015 |
| IIY4938 | 14 | 2771681 |
| IIY4953 | 14 | 2926741 |
| IIY20325 | 14 | 3106964 |
| IIY4978 | 14 | 3127412 |
| IIY4994 | 14 | 3412862 |
| IIY5036 | 14 | 3825644 |
| IIY15710 | 14 | 4236984 |
| IIY5126 | 14 | 4655438 |
| IIY5180 | 14 | 4857870 |
| IIY5182 | 14 | 4861117 |
| IIY5223 | 14 | 5001537 |
| IIY428 | 14 | 5028572 |
| IIY5226 | 14 | 5040236 |
| IIY19806 | 14 | 17652349 |
| IIY19935 | 14 | 19494194 |
| IIY4944 | 14 | 28146341 |
| IIY20580 | 15 | 2316022 |
| IIY5554 | 15 | 2805463 |
| IIY20067 | 15 | 3796702 |
| IIY5625 | 15 | 4108526 |
| IIY20290 | 15 | 4174719 |
| IIY6133 | 16 | 25570 |
| IIY6561 | 16 | 60477 |
| IIY6594 | 16 | 68850 |
| IIY6642 | 16 | 95735 |
| IIY6112 | 16 | 231562 |
| IIY6131 | 16 | 253889 |
| IIY6376 | 16 | 348886 |
| IIY6536 | 16 | 465392 |
| IIY6050 | 16 | 1312414 |
| IIY6053 | 16 | 1346152 |
| IIY15765 | 16 | 1358540 |
| IIY6226 | 16 | 3057779 |
| SY2898 | 16 | 3560231 |
| IIY6446 | 16 | 3648660 |
| IIY6512 | 16 | 3887097 |
| IIY18435 | 16 | 3964335 |
| IIY18546 | 16 | 4825835 |
| IIY14795 | 16 | 5384269 |
| IIY18907 | 16 | 6125865 |
| IIY6564 | 16 | 6247202 |
| IIY6567 | 16 | 6411631 |
| IIY6603 | 16 | 7287728 |
| IIY18918 | 16 | 18715395 |
| IIY6989 | 17 | 414639 |
| IGGY1878 | 17 | 691058 |
| IIY20836 | 17 | 1132147 |
| IGGY131 | 17 | 5141900 |
| IIY7134 | 17 | 8109126 |
| IIY8052 | 18 | 926063 |
| IIY16693 | 18 | 993080 |
| IIY7218 | 18 | 1087302 |
| IIY21953 | 18 | 1107973 |
| IIY21085 | 18 | 1140731 |
| IIY7234 | 18 | 1156406 |
| IGGY444 | 18 | 1229025 |
| IIY7269 | 18 | 1376711 |
| IIY7292 | 18 | 1541073 |
| IIY7294 | 18 | 1544945 |
| IIY22231 | 18 | 1638718 |
| IIY7315 | 18 | 1686815 |
| IIY7317 | 18 | 1690011 |
| IGGY2342 | 18 | 1712035 |
| IIY14734 | 18 | 1736100 |
| IIY7321 | 18 | 1769041 |
| IIY7373 | 18 | 2154488 |
| IIY8133 | 19 | 2130765 |
| IIY1577 | 19 | 4141465 |
| IIY21405 | 19 | 7897176 |
| IIY21406 | 19 | 8023757 |
| IIY8166 | 19 | 31003233 |
| IIY8278 | 19 | 39440215 |
| IIY21959 | 19 | 39676454 |
| IIY8287 | 19 | 39733215 |
| IIY1594 | 19 | 39921349 |
| IIY14726 | 19 | 40774016 |
| IIY8326 | 19 | 40779456 |
| IIY8337 | 19 | 41332455 |
| IIY8339 | 19 | 41341024 |
| IIY8342 | 19 | 41722212 |
| IIY857 | 19 | 42821675 |
| IIY9566 | 20 | 34401254 |
| IIY9631 | 20 | 35770280 |
| IIY9645 | 20 | 35929462 |
| IIY21710 | 20 | 36062846 |
| IIY9685 | 20 | 36462133 |
| IIY15282 | 15 | 9652022 |
| IIY15157 | 15 | 9777403 |
| IIY6009 | 15 | 9779127 |
| IIY6017 | 15 | 9860854 |
| IIY6020 | 15 | 9907375 |
| IIY5335 | 15 | 10437176 |
| IIY5359 | 15 | 11416165 |
| IIY3392 | 12 | 115957 |
| IIY3538 | 12 | 297849 |
| IIY3998 | 12 | 994443 |
| IIY3382 | 12 | 1112602 |
| IIY3450 | 12 | 1827361 |
| IIY3495 | 12 | 2385732 |
| IIY151 | 12 | 2681306 |
| IIY3532 | 12 | 2888033 |
| IGGY174 | 12 | 3143935 |
| IIY3571 | 12 | 3203743 |
| IIY1395 | 12 | 4647654 |

In some embodiments, any one of the marker allele(s) associated with iron deficiency chlorosis are as set forth in Tables 1 or 2 may be used to identify, select or produce a plant having tolerance to iron deficiency chlorosis.

As would be understood by one of skill in the art, additional chromosomal intervals can be defined by the SNP markers provided herein in Tables 1 or 2.

This invention further provides methods of identifying, selection, and/or producing an iron deficiency chlorosis (IDC) tolerant soybean plant or part thereof, comprising: detecting, in said soybean plant or part thereof, the presence of any combination of genetic markers associated with IDC tolerance in a soybean plant, as described in Tables 1 or 2.

In further embodiments, the marker can comprise, consist essentially of or consist of any marker linked to the aforementioned markers. That is, any genetic marker that is in linkage disequilibrium with any of the aforementioned markers, as described in Table. SNPs, chromosome intervals and/or combinations of markers (haplotypes)) may also be used to identify, select and/or produce a soybean plant having IDC tolerance. Linked markers may be determined, for example, by using resources available on the SoyBase website (soybase.org).

The present invention further provides that the detecting of a molecular marker can comprise the use of a nucleic acid probe having a nucleotide base sequence that is substantially complementary to the nucleic acid sequence defining the genetic marker and which nucleic acid probe specifically hybridizes under stringent conditions with a nucleic acid sequence defining the genetic marker. A suitable nucleic acid probe can for instance be a single strand of the amplification product corresponding to the marker. In some embodiments, the detecting of a marker is designed to determine whether a particular allele of an SNP is present or absent in a particular plant.

Additionally, the methods of this invention include detecting an amplified DNA fragment associated with the presence of a particular allele of an SNP, for example as those SNP allele markers identified in Table 1. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (i.e., has a homology of in some embodiments more than 80%, in some embodiments more than 90%, in some embodiments more than 95%, in some embodiments more than 97%, and in some embodiments more than 98% or 99%) to the expected sequence based on the sequence of the marker associated with that SNP in the plant in which the marker was first detected.

The detection of an amplified DNA fragment having the predicted length or the predicted nucleic acid sequence can be performed by any of a number or techniques, including, but not limited to, standard gel-electrophoresis techniques or by using automated DNA sequencers. These methods are not described here in detail as they are well known to those of ordinary skill in the art, although exemplary approaches are set forth in the Examples.

As shown in Table 1, the SNP markers of this invention are associated with IDC tolerance. In some embodiments, as described herein, one marker or a combination of markers can be used to detect the presence of an IDC tolerant plant. In some embodiments, a marker can be located within a chromosomal interval (e.g. QTL) or be present in the genome of the plant as a haplotype as defined herein.

Thus, methods for identifying and/or selecting a soybean plant or germplasm comprising IDC tolerance comprise detecting the presence of a genetic marker (e.g., SNP, SNP located in chromosomal interval (QTL) and/or combination of SNPs) associated with IDC tolerance in a soybean plant or part thereof. Thus, the genetic marker can be detected in any sample taken from the soybean plant or from a soybean germplasm, including, but not limited to, the whole plant or germplasm or any part thereof (e.g., a seed, a leaf, a tissue culture, a cell, etc.).

In another aspect of the invention, a method of identifying and/or selecting an iron deficiency chlorosis (IDC) tolerant soybean plant or part thereof is provided, the method comprising: detecting, in said soybean plant or part thereof, the presence of a marker associated with IDC tolerance (e.g as shown in Table 1) in a soybean plant, wherein the IDC tolerance is exhibited as reduced yellow flash symptoms.

In other embodiments of this invention, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant (e.g. such as those described in Table 1), wherein the IDC tolerance is exhibited as reduced yellow flash symptoms, and the marker is associated with reduced yellow flash symptoms in a soybean plant.

In a further aspect, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as recovery from yellow flash, and the marker is associated with recovery from yellow flash in a soybean plant and is located within a chromosomal interval of: chromosomal interval on chromosome 5 defined by and including a T allele at IIY12124, a G allele at IIY12130, a A allele at IIY12132 or any combination thereof; (b) a chromosomal interval on chromosome 7 defined by and including a A allele at IIY13279, a G allele at SY0106A, a G allele at SY0642A, or any combination thereof; (c) a chromosomal interval on chromosome 13 defined by and including a C allele at SY0132A, a A allele at SY1091A, or any combination thereof; and (k) any combination of (a) through (c) and selecting a progeny soybean plant or germplasm that possesses said marker within its genome, thereby identifying and/or selecting an IDC tolerant soybean plant or part thereof.

In a further aspect, a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as recovery from yellow flash, and the marker is associated with recovery from yellow flash in a soybean plant and is located within a chromosomal interval of as indicated by any combination of one or more SNP markers as indicated in Tables 1 or 2.

The present invention additionally provides a method of identifying and/or selecting an iron deficiency chlorosis (IDC) tolerant soybean plant or part thereof, the method comprising: detecting, in said soybean plant or part thereof, the presence of a marker associated with IDC tolerance in a soybean plant, wherein the IDC tolerance is exhibited as recovery from yellow flash, and the marker is associated with recovery from yellow flash in a soybean plant.

Another embodiment of the invention comprises the use of one or more markers to identify, select or create a soybean plant that are tolerant or nontolerant (listed respectfully "tolerant allele or intolerant allele) to IDC the one or more markers selected from the group consisting of the following alleles: (a) a A allele at IIY712: (b) a A allele at SY0622A; (c) a G allele at SY0023A; (d) an T allele at IIY9605; (e) a T allele at IIY12124: (f) a G allele at IIY12132; (g) a G allele at IIY12130; (h) a A allele at IIY13279; (i) a G allele at SY0106A; (j) a G allele at SY0642A; (k) a C allele at SY0132A; (l) a A allele at SY1091A; (m) a A allele at IIY16255; (n) a A allele at IIY6614; (o) a A allele at IIY6608; (p) a G allele at IIY6613; and any combination of (a) through (p) above In another aspect of the invention a method of identifying and/or selecting an iron deficiency chlorosis (IDC) tolerant soybean plant or part thereof is provided, the method comprising: detecting, in said soybean plant or part thereof, the presence of a marker associated with IDC tolerance in a soybean plant, wherein the IDC tolerance is exhibited as reduced yellow flash and recovery from yellow flash, and the marker is associated with reduced yellow flash and recovery from yellow flash in a soybean plant and is associated with an allele comprising: (a) a A allele at IIY712; (b) a A allele at SY0622A; (c) a G allele at SY0023A; (d) an T allele at IIY9605; (e) a T allele at IIY12124; (f) a G allele at IIY12132; (g) a G allele at IIY12130; (h) a A allele at IIY13279; (i) a G allele at SY0106A; (j) a G allele at SY0642A; (k) a C allele at SY0132A; (l) a A allele at SY1091A: (m) a A allele at IIY16255; (n) a A allele at IIY6614; (o) a A allele at IIY6608; (p) a G allele at IIY6613; and any combination of (a) through (p) above.

In one embodiment, one may select for IDC markers within specific regions of the Soybean genome these regions comprise (+/−10-20 nucleotides from each relative position within said interval) (a) a chromosomal interval consisting of positions 4.94 to 6.15 on Soybean chromosome 5; (b) a chromosomal interval consisting of positions 7.04-26.97 on Soybean chromosome 14; (c) a chromosomal interval consisting of positions 32.70-36.69 on Soybean chromosome 6; (d) a chromosomal interval consisting of positions 72.72 or 93.69 on Soybean chromosome 1; (e) a chromosomal interval consisting of positions 22.10-54.83 on Soybean chromosome 2; (f) a chromosomal interval consisting of positions 99.70-132.16 on Soybean chromosome 17; (g) a chromosomal interval consisting of positions 31.99-95.92 on Soybean chromosome 15; (h) a chromosomal interval consisting of positions 77.49-92.55 on Soybean chromosome 13; (i) a chromosomal interval consisting of positions 127.05-129.01 on Soybean chromosome 18; (j) a chromosomal interval consisting of positions 91.92-117.61 on Soybean chromosome 12; (k) a chromosomal interval consisting of positions 69.90-75.67 on Soybean chromosome 9; (l) a chromosomal interval consisting of positions 65.52-69.09 on Soybean chromosome 19; (m) a chromosomal interval consisting of positions 105.76-113.05 on Soybean chromosome 3; (n) a chromosomal interval consisting of position 116.87 on Soybean chromosome 10 and (o) any combination of markers selected from the chromosome intervals as stated in (a)-(n) above.

As described herein, methods for identifying and/or selecting a soybean plant or germplasm having IDC tolerance can comprise detecting the presence of a marker or a combination of markers associated with IDC tolerance. Any combination of the genetic markers of this invention can be used to identify and/or select a soybean plant or germplasm having IDC tolerance.

As described herein, in some aspects of this invention, the reduced yellow flash symptoms and/or recovery from yellow flash are exhibited by the soybean plant when the soybean plant is grown in calcareous soil having a pH greater than 7.5 and the marker is associated with reduced yellow flash symptoms and/or recovery from yellow flash in a soybean plant when the soybean plant is grown in calcareous soil having a pH greater than 7.5. In other embodiments the markers may be used to select, identify, and introgress IDC tolerant soy line in either soil type 1 or soil type 2.

Accordingly, some embodiments of the present invention provide a method of identifying and/or selecting an iron deficiency chlorosis (IDC) tolerant soybean plant, wherein the IDC tolerance is exhibited as reduced yellow flash symptoms and/or recovery from yellow flash when the plant is grown calcareous soil having a pH greater than 7.5, and the marker (e.g., SNP allele, combination of SNP alleles and/or SNP allele located in a chromosome interval) is associated with reduced yellow flash symptoms and/or recovery from yellow flash in a soybean plant grown in calcareous soil having a pH greater than 7.5.

Marker-Assisted Selection

The subject matter disclosed herein also relates to methods for producing IDC tolerant soybean plants comprising detecting the presence of an allele associated with IDC tolerance in a donor soybean plant according to the methods as described herein and transferring a nucleic acid sequence comprising at least one allele thus detected from the donor plant to an IDC intolerant recipient soybean plant. The transfer of the nucleic acid sequence can be performed by any of the methods described herein.

Thus, the present invention encompasses methods of plant breeding and methods of selecting/identifying plants, in particular soybean plants, particularly cultivated soybean plants as breeder plants for use in breeding programs or cultivated soybean plants having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example, a plant obtained by inbreeding. It is also understood by those skilled in the an that it is of equal value to be able to select for plants that are not tolerant to IDC in for example, a Soybean plant breeding program.

The presently disclosed subject matter thus also provides methods for selecting a plant of the genus *Glycine* exhibiting tolerance to iron deficiency chlorosis (IDC) comprising detecting in the plant the presence of one or more genetic markers associated with IDC tolerance as defined herein. In an exemplary embodiment of the presently disclosed methods for selecting such a plant, the method comprises providing a sample of genomic DNA from a soybean plant; and (b) detecting in the sample of genomic DNA at least one genetic marker associated with IDC tolerance. In some embodiments, the detecting can comprise detecting one or more SNPs, a combination of SNPs (haplotype), and/or SNPs located in chromosomal intervals that are associated with IDC tolerance.

The providing of a sample of genomic DNA from a soybean plant can be performed by standard DNA isolation methods well known in the art.

As is well known in the art, the detecting of a genetic marker can in some embodiments comprise the use of one or more sets of primer pairs that can be used to produce one or more amplification products that are suitable for identifying, for example, a SNP. In exemplary embodiments of this invention, the nucleotide sequences comprising the genetic markers (SNPs) and probes for the detection of respective markers are provided in Table 1.

In some embodiments of this invention, a method is provided, said method comprising the transfer by introgression of the nucleic acid sequence from an IDC tolerant donor soybean plant into an IDC intolerant recipient soybean plant by crossing the plants. This transfer can be accomplished by using traditional breeding techniques. IDC tolerant loci are introgressed in some embodiments into commercial soybean varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode for the desired trait. As disclosed herein, such identification and selection is based on selection of one or more SNP alleles of this invention or markers associated therewith. MAB can also be used to develop near-isogenic lines (NIL) harboring one or more IDC tolerance alleles of interest, allowing a more detailed study of an effect of such allele(s), and is also an effective method for development of backcross inbred line (BIL) populations. Soybean plants developed according to these embodiments can in some embodiments derive a majority of their traits from the recipient plant and derive IDC tolerance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with IDC tolerance into an IDC intolerant recipient soybean plant. For example, inbred IDC tolerant soybean plant lines can be developed using the techniques of recurrent selection and backcrossing, selfing, and/or dihaploids, or any other technique used to make parental lines. In a method of recurrent selection and backcrossing, IDC tolerance can be introgressed into a target recipient plant (the recurrent parent) by crossing the recurrent parent with a first donor plant, which differs from the recurrent parent and is referred to herein as the "non-recurrent parent." The recurrent parent is a plant that is IDC intolerant or has a low level of IDC tolerance and, in some embodiments, possesses commercially desirable characteristics, such as, but not limited to disease and/or insect resistance, valuable nutritional characteristics, valuable abiotic stress tolerance (including, but not limited to, drought tolerance, salt tolerance), and the like. In some embodiments, the non-recurrent parent exhibits IDC tolerance and comprises a nucleic acid sequence that is associated with IDC tolerance. The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence associated with IDC tolerance. Also, MAB can be used to confirm the results obtained from the quantitative bioassays. In some embodiments, the markers defined herein are suitable to select proper offspring plants by genotypic screening.

Following screening, the F1 hybrid plants that exhibit an IDC tolerance phenotype or, in some embodiments, the genotype, and thus comprise the requisite nucleic acid sequence associated with IDC tolerance, can be then selected and backcrossed to the recurrent parent for one or more generations in order to allow for the soybean plant to become increasingly inbred. This process can be performed for one, two, three, four, five, six, seven, eight, or more generations.

Thus, a marker that demonstrates linkage with a locus affecting a desired phenotypic trait provides a useful tool for selection of the trait in a plant population. This is particularly true where the phenotype is hard to assay or occurs at a late stage in plant development. Since DNA marker assays are less laborious and take up less physical space than field phenotyping, much larger populations can be assayed, increasing the chances of finding a recombinant plant with the target segment from the donor line moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the soybean genome containing increasing densities of public soybean markers has facilitated soybean genetic mapping and MAS. See, e.g. soybeanbreederstoolbox.org, which can be found on the SoyBase website (soybase.org).

Of all the molecular marker types, SNPs are the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: *Gut, Hum. Mutat.* 17:475 (2001); *Shi. Clin. Chem.* 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman™ (Applied Biosystems, Foster City, Calif.) and Beadarrays™ (Illumina, San Diego, Calif.).

Accordingly, the markers of the present invention can be used in marker-assisted selection methods to identify and/or select and/or produce progeny having a genetic marker associated with IDC tolerance. Thus, in some embodiments, the present invention relates to methods for producing soybean plants having an IDC tolerance associated allele comprising detecting the presence of at least one allele associated with IDC tolerance in a donor soybean plant as described herein, crossing the donor soybean plant with a second soybean plant or germplasm, and detecting in the progeny plant(s) the presence of said at least one allele, thereby transferring the at least one allele thus detected from the donor plant to the second soybean plant and thus producing a soybean plant having IDC tolerance. In some embodiments, the second plant is IDC intolerant. The transfer of the allele can be performed by any of the methods described herein.

Embodiments of the invention provides a method of identifying, selecting or producing an iron deficiency chlorosis (IDC) tolerant soybean plant through any one or a combination of the markers as set forth in Table 2.

One embodiment of the invention is the use of at least one marker from Table 1 associated with IDC in a soybean plant breeding program.

In some embodiments, the second soybean plant or germplasm of this invention is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean.

In other embodiments, the present invention provides a method of introgressing a combination of genetic markers associated with iron deficiency chlorosis (IDC) tolerance into a genetic background lacking said combination of markers, comprising: crossing a donor comprising said combination of markers with a recurrent parent that lacks said combination of markers; and backcrossing progeny comprising said combination of markers with the recurrent parent, wherein said progeny are identified by detecting, in their genomes, the presence of said combination of markers associated with IDC tolerance in a soybean plant, wherein said combination of genetic markers comprises any marker shown in Tables 1 or 2 and any combination thereof, thereby producing an IDC tolerant soybean plant or germplasm comprising said combination of markers associated with IDC tolerance in the genetic background of the recurrent parent, thereby introgressing the combination of markers associated with IDC tolerance into a genetic background lacking said combination of markers.

Accordingly, some embodiments of the present invention provide a method of producing and/or selecting an iron deficiency chlorosis (IDC) tolerant soybean plant, wherein the IDC tolerance is exhibited as reduced yellow flash symptoms and/or recovery from yellow flash when the plant is grown in calcareous soil having a pH greater than 7.5, and the marker (e.g., SNP allele, combination of SNP alleles, SNP allele located in a chromosome interval) is associated with reduced yellow flash symptoms and/or recovery from yellow flash in a soybean plant grown in calcareous soil having a pH greater than 7.5. In other aspects the markers may be used to identify, create or select soy lines that may be grown on soil type 1, soil type 2 or both.

The present invention provides soybean plants and germplasms having IDC tolerance. As discussed above, the methods of the present invention can be utilized to identify, produce and/or select a soybean plant or germplasm having IDC tolerance. In addition to the methods described above, a soybean plant or germplasm having IDC tolerance may be produced by any method whereby a marker associated with IDC tolerance (for example any one or more of the markers identified in Table 1) is introduced into the soybean plant or germplasm by such methods that include, but are not limited to, transformation (including, but not limited to, bacterial-mediated nucleic acid delivery (e.g., via Agrobacteria)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof), protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part ("Introducing" encompasses introgression, gene editing and/or transgenic expression). Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a soybean plant, or part thereof, having a genetic marker associated with IDC tolerance, obtainable by the methods of the presently disclosed subject matter, are aspects of the presently disclosed subject matter. The soybean plant, or part thereof, or soybean germplasm of this invention having a genetic marker associated with IDC tolerance can be heterozygous or homozygous for the genetic marker.

In some embodiments, the soybean plant or germplasm may be the progeny of a cross between an elite variety of soybean and a variety of soybean that comprises an allele associated with IDC tolerance. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The soybean plant or germplasm may be the progeny of an introgression wherein the recurrent parent is an elite variety of soybean and the donor comprises a genetic marker associated (e.g., SNP, combination of SNPs, SNP located in a chromosome interval) with IDC tolerance as described herein (e.g. such as markers disclosed in Table 1).

The soybean plant or germplasm may be the progeny of a cross between a first elite variety of soybean (e.g., a tester line) and the progeny of a cross between a second elite variety of soybean (e.g., a recurrent parent) and a variety of soybean that comprises a genetic marker associated with IDC tolerance as described herein (e.g., a donor).

The soybean plant or germplasm may be the progeny of a cross between a first elite variety of soybean and the progeny of an introgression wherein the recurrent parent is a second elite variety of soybean and the donor comprises a genetic marker associated with IDC tolerance.

Another aspect of the presently disclosed subject matter relates to a method of producing seeds that can be grown into IDC tolerant soybean plants. In some embodiments, the method comprises providing an IDC tolerant soybean plant of this invention (e.g. via use of IDC markers as disclosed in Table 2), crossing the IDC tolerant soybean plant with another soybean plant, and collecting seeds resulting from the cross, which when planted, produce IDC tolerant soybean plants.

Accordingly, the present invention provides improved soybean plants, seeds, and/or soybean tissue culture produced by the methods described herein.

In some embodiments, the presently disclosed subject matter provides methods for analyzing the genomes of soybean plants/germplasms to identify those that include desired markers associated with IDC tolerance. In some embodiments, the methods of analysis comprise amplifying subsequences of the genomes of the soybean plants/germplasms and determining the nucleotides present in one, some, or all positions of the amplified subsequences.

Thus, in some embodiments, the present invention provides compositions comprising one or more amplification primer pairs capable of initiating DNA polymerization by a DNA polymerase on a *Glycine max* nucleic acid template to generate a *Glycine max* amplicon. In some embodiments, the *Glycine max* marker amplicon corresponds to *Glycine max* marker comprising a nucleotide sequence of any of SEQ ID NOs: 1-16. In view of the disclosure of SEQ ID NOs: 1-16 being linked to IDC tolerance loci, one of ordinary skill in the art would be aware of various techniques that could be employed to analyze the sequences of the corresponding soybean nucleic acids.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1. QTL Mapping and Phenotyping Soybean Plant Material

Syngenta soybean plant materials were used to develop the iron deficiency chlorosis (IDC) quantitative trait loci (QTL) mapping populations. The parent populations were either IDC tolerant or IDC intolerant soybean materials based upon phenotyping of the population and knowledge of the germplasm. The parent materials classifications are provided in Table 2.

A connected structure of populations was fashioned from the parent materials. Tables 3a and 3b shows the generation, harvest method, timeline, and nursery location of the QTL population. Finally, checks were chosen based upon breeding experience and product knowledge. The phenotyping check populations are listed in Table 4.

TABLE 3a

| Parent materials classifications | |
|---|---|
| Parental Material | IDC Tolerance Classification |
| 03D1052038 | Tolerant |
| 04K1108888 | Tolerant |
| 9378 | Intolerant |
| 1162 | Intolerant |
| 9478 | Intolerant |
| 5763 | Intolerant |

TABLE 3a-continued

| Parent materials classifications | |
|---|---|
| Parental Material | IDC Tolerance Classification |
| 1519 | Intolerant |
| 1531 | Intolerant |

TABLE 3b

| Population development | | |
|---|---|---|
| Generation | Harvest Method | Timeline |
| Crossing | Bulk | Summer Year 1 |
| F1 Plants | Bulk | Fall Year 1-Winter Year 2 |
| F2 Plants | SSD* | Spring Year 2 |
| F3 Plants | SSD* | Summer Year 2 |
| F4 Plants | Plant pull | Fall Year 2-Winter Year 3 |

*SSD = Single Seed Descent

TABLE 4

| IDC phenotyping of check populations | |
|---|---|
| Tolerant Checks | Intolerant Checks |
| 03DL052038 | 1107 |
| 2251 | 8295 |
| 4015 | 8413 |
| 8047 | 8851 |
| 0011 | 1285 |

Example 2. Experiment Design and Phenotyping

The eleven F4 populations were arranged into eleven—two replicate, three location, IDC phenotyping experiments. The same ten phenotyping checks/controls were used in all experiments. The experimental design was Randomized Complete Block (RCB), which also included a repeating intolerant check (material 8314) occurring every 10th hill.

The three planting locations were used: Truman, Minn.; Ogden, Iowa; and Fort Dodge, Iowa. The field area at each site was prepared with a 48 inch wide rotary tiller just prior to planting to remove compaction.

The plots were kept weed free throughout the life of the experiment; however, no Post-Emergence herbicide was used. The planter's four row units were spaced 10 inches apart and the hills were placed every 15 inches down the row to minimize the field size needed. Six seeds per hill (replicates) were planted. The 12 experiments were contiguously arranged in a block. Experimental replicates were blocked and mapped adjacent to each other. The hills within replicates were arranged in a serpentine fashion Plants were evaluated for IDC visually and by electronic scanning (radiometer). Table 5, below, summarizes the trait codes, description, type, minimum and maximum values for each type of measurement, and the calculation (formula) when applicable that were used in the evaluations. At approximately the V2 stage of growth, the hills were visually rated and canopy reflectance measured (or NDVI (Normalized Difference Vegetation Index)) with a Greenseeker®

RT100 radiometer. The visual rating and NDVI measurement were repeated 14 days later. These times, V2 stage and 14 days later, correspond to IDC yellow flash symptom and recovery reaction times, respectively.

As shown in Table 5, ICFLR and ICFLN are codes that identify the Yellow Flash ratings for visual and radiometer, respectively. Likewise, ICR_R and ICR_N are codes that identify the Recovery for the visual ratings and the radiometer number, respectively. IC_R and IC_N are codes that identify the mean of the yellow flash and recovery data for the visual ratings and the radiometer number, respectively. The visual ratings scale was 1-9 with 1 being the best (no chlorosis) and 9 being the worst (plant death). Arithmetic averages of the visual and radiometer traits were calculated. Table 6 shows the results of a single experiment.

TABLE 5

Phenotyping Traits

| Trait Code | Description | Type of Measurement | Type of Measurement* | Minimum Value | Maximum Value | Calculation |
|---|---|---|---|---|---|---|
| IC_N | Mean of Flash and Recovery | Radiometry | Measured | 0 | 1 | ICFLN + ICR_N)/2 |
| IC_R | Mean of Flash and Recovery | Visual | Measured | 1 | 9 | ICFLR + ICR_R)/2 |
| IC_AN | Mean of Flash and Recovery | Radiometry | Adjusted | 0 | 1 | ICFAN + ICR_AN)/2 |
| IC_AR | Mean of Flash and Recovery | Visual | Adjusted | 1 | 9 | ICFAR + ICR_AR)/2 |
| ICFAN | Flash | Radiometry | Adjusted | 0 | 1 | |
| ICFAR | Flash | Visual | Adjusted | 1 | 9 | |
| ICFLN | Flash | Radiometry | Measured | 0 | 1 | |
| ICFLR | Flash | Visual | Measured | 1 | 9 | |
| ICR_N | Recovery | Radiometry | Measured | 0 | 1 | |
| ICR_R | Recovery | Visual | Measured | 1 | 9 | |
| ICRAN | Recovery | Radiometry | Adjusted | 0 | 1 | |
| ICRAR | Recovery | Visual | Adjusted | 1 | 9 | |

*Indicates whether the phenotypic data was adjusted by the surface analysis utility as discussed in Example 5.

TABLE 6

Phenotyping results from a single experiment (sorted by IC_R).

| | | Visual | | | Radiometer | | |
|---|---|---|---|---|---|---|---|
| ENTRY | Material | IC_R | ICFLR | ICR_R | IC_N | ICFLN | ICR_N |
| 42 | 03DL052038 Tolerant Control | 1.7 | 2.2 | 0.6 | 0.474 | 0.441 | 0.514 |
| 21 | | 2 | 2.5 | 0.9 | 0.473 | 0.466 | 0.509 |
| 3 | | 2.2 | 2.7 | 0.9 | 0.455 | 0.399 | 0.514 |
| 20 | | 2.2 | 2.9 | 0.6 | 0.415 | 0.408 | 0.452 |
| 37 | 2251 Tolerant Control | 2.2 | 2.5 | 1.3 | 0.469 | 0.447 | 0.507 |
| 16 | | 2.7 | 2.4 | 2.3 | 0.454 | 0.45 | 0.495 |
| 44 | 4015 Tolerant Control | 3 | 3 | 1.9 | 0.415 | 0.398 | 0.49 |
| 8 | | 3 | 3.7 | 1.3 | 0.447 | 0.453 | 0.475 |
| 39 | 8047 Tolerant Control | 3 | 3.5 | 1.6 | 0.389 | 0.376 | 0.457 |
| 31 | | 3.5 | 4 | 1.9 | 0.433 | 0.369 | 0.495 |
| 14 | | 3.7 | 4.4 | 1.6 | 0.448 | 0.444 | 0.48 |
| 33 | 0011 Tolerant Control | 3.7 | 3.1 | 3.6 | 0.171 | 0.177 | 0.164 |
| 13 | | 3.8 | 4.5 | 1.9 | 0.397 | 0.392 | 0.445 |
| 30 | | 3.8 | 4.2 | 2.6 | 0.308 | 0.382 | 0.276 |
| 22 | | 4 | 4.3 | 2.6 | 0.398 | 0.404 | 0.437 |
| 35 | | 4 | 4.1 | 2.6 | 0.462 | 0.469 | 0.508 |
| 7 | | 4.3 | 3.7 | 3.9 | 0.435 | 0.468 | 0.455 |
| 5 | | 4.3 | 4.2 | 3.3 | 0.379 | 0.417 | 0.38 |
| 10 | | 4.3 | 4.5 | 3.3 | 0.395 | 0.417 | 0.409 |
| 15 | | 4.5 | 4.4 | 3.3 | 0.417 | 0.435 | 0.461 |
| 19 | | 4.5 | 4.8 | 2.9 | 0.383 | 0.388 | 0.425 |
| 4 | | 4.7 | 4.8 | 3.6 | 0.37 | 0.368 | 0.397 |
| 6 | | 4.7 | 5 | 2.9 | 0.275 | 0.43 | 0.173 |
| 24 | | 4.7 | 4.2 | 3.9 | 0.319 | 0.382 | 0.351 |
| 18 | | 5 | 5.2 | 3.6 | 0.322 | 0.351 | 0.337 |
| 2 | | 5.2 | 5.2 | 3.9 | 0.355 | 0.383 | 0.408 |
| 32 | | 5.3 | 4.7 | 4.6 | 0.319 | 0.378 | 0.345 |
| 36 | | 5.3 | 5.2 | 4.3 | 0.23 | 0.283 | 0.2 |
| 9 | | 5.5 | 5 | 4.6 | 0.397 | 0.365 | 0.461 |
| 17 | | 5.5 | 4.5 | 5.3 | 0.336 | 0.352 | 0.371 |
| 27 | | 5.5 | 4.7 | 4.9 | 0.38 | 0.41 | 0.417 |

TABLE 6-continued

Phenotyping results from a single experiment (sorted by IC_R).

| ENTRY | Material | Visual | | | Radiometer | | |
|---|---|---|---|---|---|---|---|
| | | IC_R | ICFLR | ICR_R | IC_N | ICFLN | ICR_N |
| 25 | | 5.8 | 5.5 | 4.6 | 0.335 | 0.378 | 0.359 |
| 28 | | 5.8 | 5 | 5.3 | 0.351 | 0.381 | 0.385 |
| 40 | 1107 Intolerant Control | 5.8 | 5.7 | 4.9 | 0.331 | 0.355 | 0.353 |
| 29 | | 6 | 6.2 | 4.6 | 0.34 | 0.367 | 0.389 |
| 11 | | 6.2 | 4.9 | 6.3 | 0.235 | 0.291 | 0.301 |
| 41 | 8295 Intolerant Control | 6.2 | 5.8 | 5.6 | 0.325 | 0.376 | 0.352 |
| 1 | 8413 Intolerant Control | 6.2 | 5.1 | 5.5 | 0.345 | 0.392 | 0.37 |
| 26 | | 6.3 | 5.2 | 5.9 | 0.224 | 0.31 | 0.255 |
| 43 | 8851 Intolerant Control | 6.3 | 5.9 | 5.9 | 0.271 | 0.322 | 0.295 |
| 38 | 1285 Intolerant Control | 6.7 | 5.5 | 6.6 | 0.238 | 0.248 | 0.257 |
| | Mean General | 4.6 | 4.4 | 3.6 | 0.362 | 0.384 | 0.391 |
| | Mean Control | 2.7 | 2.9 | 1.8 | 0.383 | 0.368 | 0.426 |
| | Trials w/data | 2 | 3 | 2 | 2 | 3 | 2 |
| | Entries w/data | 41 | 41 | 41 | 41 | 41 | 41 |
| | LSD General (5%) EE | 2 | 1.5 | 2.8 | 0.161 | 0.106 | |
| | LSD* Control (5%) EC | 1.5 | 1.1 | 2.1 | 0.125 | 0.082 | |
| | CV** (Effective) % | 22 | 19.1 | 39.4 | 22.175 | 16.957 | 31.129 |

*LSD = Least significant different;
**CV = Coefficient of Variation

The IDC phenotyping results in Table 6 indicate that at 95% confidence level, significant differences were detected between materials/entries. LSD General (5%) EE and LSD Control (5%) EC statistics allow entry to entry or entry to control comparisons, respectively. The results also indicate that significant differences are detected in the traits within visual and radiometer phenotyping.

Example 3. Classification of IDC Prone Soils

Soil samples were collected from eight IDC phenotyping locations in Nebraska, Iowa, Minnesota and North Dakota. These samples were collected from field spots in which non-IDC tolerant soybean plants show IDC symptoms. These soils samples were analyzed for standard soil nutrients, salts, and pH at Mid-West Laboratories, Omaha NB. The data from these soil samples was analyzed for Principal Component Analysis (PCA). PCA is a multivariate analysis which can be used to reveal patterns or clusters in multivariate data. Principal component 1 and Principal component 2 revealed two main distinct clusters for these soil samples. Soils samples collected from Iowa-Southern Minnesota and North Dakota-Northern Minnesota were grouped in two distinct clusters (soil type 1 and soil type 2 respectively). A location from Nebraska did not group with any of these two clusters. This analysis indicated that soil conditions and their properties which cause IDC can be grouped into three classes—Iowa-Southern Minnesota type soils. North Dakota-Northern Minnesota type soils and Nebraska type soils.

Example 4. Genotyping of the IDC QTL Population

All parents of the populations identified in Example 1 were fingerprinted with genome wide SNP markers. The fingerprinting data on the parents was used to determine polymorphic SNPs for each population. Only suitable polymorphic SNPs were genotyped for each population. Table 7 provides the number of markers used to genotype each population.

TABLE 7

The number of genotyping markers.

| Population Number | Pedigree | Number of recombinant inbred lines (RILs) | Number of SNPs |
|---|---|---|---|
| 1 | 04KL108888/9428 | 60 | 193 |
| 2 | 04KL108888/1162 | 29 | 195 |
| 3 | 9378/03DL052038 | 80 | 192 |
| 4 | 5763/03DL052038 | 81 | 202 |
| 5 | 1519/03DL052038 | 53 | 147 |
| 6 | 9428/03DL052038 | 52 | 183 |
| 7 | 1531/03DL052038 | 64 | 153 |
| 8 | 1162/1519 | 85 | 199 |
| 9 | 9378/9428 | 45 | 54 |
| 10 | 1531/9378 | 83 | 132 |
| 11 | 1531/1162 | 41 | 132 |

The tissue of recombinant inbred lines (RILs) was obtained by growing them in the field or greenhouse. DNA was extracted from the leaf tissue of 7-10 day old seedlings (7-10 days after planting). DNA can be extracted from plant tissue in any way known in the art, including the CTAB (hexadecyltrimethylammonium bromide) method (See, e.g., Stewart et al., *BioTechniques* 14(5):748-749 (1993)), sodium hydroxide, and the Dellaporta method (Dellaporta et al., Plant Mol. Biol. Rep. 1:19-21 (1983)). See also, Sambrook & Russell *Molecular Cloning: A Laboratory Manual, Third Edition,* Cold Spring Harbor Laboratory Press, Cold Spring Harbor, N.Y., United States of America (2001)) for additional DNA extraction methods. DNA is diluted in TE buffer and stored at 4° C. until used in PCR reactions as described below in Table 8.

TABLE 8

PCR was set up in 5 μl final volumes according to the following formula.

| Reagent | Stock concentration | Per reaction (μl) | For 96 samples (μl) | Final concentration |
|---|---|---|---|---|
| 2X Master Mix (JumpStart ™ Taq ReadyMix ™) | 2X | 2.5 | 296.88 | 1X |
| AbD primer/probe mix (80x) | 40x | .0625 | 6 | 0.5x |
| PCR-quality H2O | — | 2.44 | 234.24 | — |
| DNA (dried in 384) | 4.5 ng/μl | 4 | — | 3.6 ng/ul (18 ng) |
| Final Volume (ul) | | 5.00 | 357.44 | |

The Master Mix is JumpStart™ Taq ReadyMix™ (Sigma Catalogue No. 2893; Sigma Chemical Co., St. Louis, Mo., United States of America), a premix of all the components, including nucleotides and Taq polymerase (but not primers and/or probes) necessary to perform a 5'-nuclease assay. Before use, 1375 μl of 1.0 M $MgCl_2$ (Sigma Catalogue No. M1028) and 250 μl of 300 μM Sulforhodamine 101 (Sigma Catalogue No. S7635), also known as ROX, are added to a 125 mL bottle of JumpStart™ Taq ReadyMix™. PCR plates were placed in an ABI 9700 thermal cycler and the program set forth in Table 9 was run:

TABLE 9

PCR program.

| Task | SNP1 |
|---|---|
| Initial denaturation | 50° C. for 2 min; followed by 95° C. for 10 min |
| Cycles | 95° C. for 15 sec<br>60° C. for 1 min |
| Number of cycles | 40 |
| Final elongation | 72° C. for 5 min |
| Hold | Hold at 4° C. |

The ABI 7900 Sequence Detection System (or Taqman®) was used to visualize the results of an allelic discrimination (SNP) assay. Using the Sequence Detection System (SDS) software, allele calls were made based on the fluorescence for the two dyes measured in each sample.

Example 5. Phenotypic Data Analysis

The raw data was analyzed using fixed effects analysis of variance (ANOVA), with the traits and populations kept separate. Populations were phenotyped with two replicates at two locations in Iowa. The model below was used, allowing testing for material ID*location interactions. Least square means within and across locations used as phenotype variables for Quantitative Trait Locus (QTL) analysis.

IDC trait=location+material ID+material ID*location+error.

Since the potential severity of IDC is related to spatially variable soil properties, statistical methods that can reduce the effects of this variability are important to increase the ability to detect QTL. Software containing a surface analysis utility was used to perform spatial adjustments based on the phenotype of a repeated check planted throughout the evaluation trial. This tool was used as a way to reduce spatial effects caused by differing potentials for IDC development across different areas of the phenotyping locations. If surface analysis could not detect the spatial patterns in phenotypic data, it returned the original, measured values. This leads to high correlations between the original measured and surface adjusted values. Therefore, comparisons between measured and surface analysis adjusted phenotype data were performed using pair-wise correlations of means across locations in the statistical analysis software package, JMP.

Across the mapping populations, 62 out of 66 comparisons (representing different combinations of IDC trait (e.g., yellow flash, recovery and mean)) had correlations of 0.98, 0.99, or 1.0. The remaining four comparisons were all from one mapping population. They had correlation coefficients ranging from 0.29 to 0.94. Regardless of the level of correlation, all traits whether surface-analyzed or from ANOVA were used in the QTL analysis.

Example 6. QTL Analysis Using Network Population Mapping (NPM)

To detect QTLs for IDC tolerance, Network Population Mapping analysis was performed using Syngenta software and analysis method (See, US Patent Publication No. 20100269216). This method is superior to standard bi-parental QTL mapping in that it uses multiple mapping populations (termed connected networks) that are designed so that the mapping parents are used in multiple populations. This design results in greater statistical power to detect QTL, since individuals across all populations are used for testing for the presence of QTL.

The population network was analyzed using the NPM method, with 1000 permutations performed to empirically determine a 0.05 significance threshold for every trait, rather than arbitrarily choosing a significance threshold. In the final analysis, trait-location combinations with very low heritability of 0.2 or less were excluded from some populations, which increased the number and significance of detected QTL.

The raw results from NPM analysis were processed using an internally developed SAS script. The output from the script was used to create summarized reports for QTL that passed the permutation test.

The network detected multiple QTL across the soy genome. Two important values in QTL studies are the LOD (logarithm of odds) and $R^2$. A higher LOD value represents greater statistical evidence for the presence of a QTL, and a higher $R^2$ indicates that the particular QTL has more effect on the trait of interest. The maximum LOD was 20.3, and the maximum $R^2$ was 0.65.

Example 7. Selecting QTL of High Confidence

From the large number of QTL observed, a subset of high confidence QTL was selected. For example, in one case, QTL could be found for only one trait-location combination at a marginal significance level, and would thus be of limited utility for marker-assisted breeding. Thus, this QTL was not included in the high confidence subset. In other cases, QTL were found that had a marginal LOD score but a suspiciously high $R^2$ value.

Thus, the following were used to prioritize QTL regions and QTL were retained if:
(1) they had a LOD score of 2.7 or greater with a reasonable $R^2$,
(2) were observed in more than one phenotyping location, or
(3) were observed for multiple correlated traits in the same genomic region at one or more phenotyping locations.

Based on the criteria outlined above, only those QTL that were of a high confidence were considered further.

Example 8. Validation of the Utility of the QTLs Associated with IDC

Eighteen candidate validation populations were made between soybean varieties to determine the utility of these QTLs in improving the tolerance to iron deficiency chlorosis in soybean.

Out of these 18 populations, 12 were selected for validation based on their relationship to the parents of the discovery populations and numbers of segregating QTL. F3 progenies of the 12 populations were genotyped as described in Example 4 using marker assays flanking QTL (only QTL of very high confidence identified in Example 7 were used).

For each population, 1380 F3 progenies were genotyped. Out of these 1380 progenies some were selected based on their QTL status. Selected progenies are evaluated for IDC at four locations in Iowa and Minnesota as per the Example 2.

Standard statistical analyses are conducted to determine the performance of the QTL in selection for progeny having tolerance to IDC.

The list of SNP markers comprising the QTL of the present invention is provided in Table 1, above. Further analysis indicated that the markers in Table 2 are further examples of markers that may associate with increased IDC tolerance.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A method of producing a soybean plant with increased tolerance to iron deficiency chlorosis (IDC), the method comprising the steps of:
   a. isolating at least one nucleic acid from a population of soybean plants;
   b. detecting in said nucleic acid a marker associated with IDC located within 5 cM of a chromosomal interval corresponding to *Glycine max* Chromosome 10 wherein said chromosomal interval comprises of SEQ ID NO: 15 and further, wherein said chromosomal interval comprises a G allele corresponding to position 251 of SEQ ID NO: 15;
   c. selecting a first soybean plant from the population of (a) based of the presence of the marker detected in (b);
   d. crossing the first soybean plant of (c) with a second soybean plant not comprising in its genome the marker detected in (b);
   e. collecting seed from the cross of (d); and
   f. growing a progeny soybean plant from the seed of (e), wherein said progeny soybean plant comprises in its genome said marker associated with increased IDC tolerance, thereby producing a plant with increased IDC tolerance.

2. The method of claim 1, wherein the marker is detected through the use of a nucleotide probe comprising a nucleotide sequence as depicted in any one of SEQ ID NOs: 84 or 85.

3. The method of claim 1, wherein the marker is detected through use of a PCR primer pair that anneals to said chromosome interval, wherein the primer pair is capable of initiating DNA polymerization by a DNA polymerase on a *Glycine max* nucleic acid template to generate a amplicon determinative for the presence of said marker associated with increased IDC tolerance.

4. The method of claim 1, wherein the progeny soybean plant is an elite soybean plant.

5. The method of claim 3, wherein the PCR primer pair comprises SEQ ID NOs: 82 and 83.

* * * * *

SEQUENCE LISTING

```
<160> NUMBER OF SEQ ID NOS: 152

<210> SEQ ID NO 1
<211> LENGTH: 408
<212> TYPE: DNA
<213> ORGANISM: Glycine max

<400> SEQUENCE: 1
tccgctgaga tcagaaggat tgagttggaa gaagtggaaa atgctaaggc taaagccaaa        60
aactttagag ggtttaggat ggaggtaatg gatgtaacaa aattagcttt gttaagacca       120
gatggtcatc ctggtgctta tatgaatcct tttccattcg ctaatggggt tccaaagcgt       180
gtgcagagtg attgtgttca ttggtgtttg ccaggaccta tagacacatg gagtgagatt       240
tttctccaga tgttrgaaaa catggcacga gcagccaagg agtgaagagt gaagcattct       300
tcatatccgt taattcattt gcaataattt tttcgccaca catgtgatgt gttgcgtcaa       360
aactagaaag agtattttgt tattttgttt gtgtgtaggt tgggctaa                    408

<210> SEQ ID NO 2
<211> LENGTH: 770
<212> TYPE: DNA
<213> ORGANISM: Glycine max
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t

<400> SEQUENCE: 2
gcaagcacat gcatcaaaca aaagtttgct aaactgctaa acgaagttcc acaatgtcaa        60
taatgtaaat cactagcaac tgaatccatc atctacaact catttcatga aataaaagtt       120
gctctacatt gtcatcttga agctcttatc ccactnttca ttgatggatg gaccaatcca       180
gtaaaaggat gaatgccgac agccacattt gctccttcaa tcccatgaaa aatattttca       240
```

```
atttgtttta gaaccaatct tcctcttagc aaaagatggc aancagaaag ccgctgtatg    300
aatctgaaat agaaaacaga caaaatataw gagtcaagta agaaaaatca gtcggatgtt    360
ttgaagttag tggaaaaaga acatggtcgg agcaacaaac ctcagagttg taaaatttca    420
atggtcttga ttgctgacta tcattctcat ttataggatt cactggatgc ttgaaatcaa    480
caagaggacc ctcagttgag caaagcataa aaccaatcat cccactgaaa tggaaataat    540
caaaaccaac ataaatatgg ttaataatat aaattctaaa cataggacta tgttttgaag    600
actgcaatgc aaatgggaaa ataatatttg aagggcata ccttgggtat gtaggaactg    660
tggtccatgc atagttgata gaacctttga atatttggcg acaattagcc acaatgtcct    720
caatgatgtg catatgaagc catatacttt ctgcttgagt acacacaact            770

<210> SEQ ID NO 3
<211> LENGTH: 121
<212> TYPE: DNA
<213> ORGANISM: Glycine max
<220> FEATURE:
<221> NAME/KEY: misc_feature
<222> LOCATION: (69)..(69)
<223> OTHER INFORMATION: n is a, c, g, or t

<400> SEQUENCE: 3
atttctccat tgtatatatg tatacaagtc aagctcttca aaaccaccaa tgcgccaatg     60
mattcaaang tgaagcgtgg tcttaaaaat tcgcatttgc ttctggccag gtctctcgtg    120
g                                                                    121

<210> SEQ ID NO 4
<211> LENGTH: 496
<212> TYPE: DNA
<213> ORGANISM: Glycine max

<400> SEQUENCE: 4
ttagctttaa aatcctcagg cttactgcca aagccttaag gtaaagaact aaaagttaca     60
agatttctca atttacacca tttactagaa tagtttgact acaaaccaaa aagcattaat    120
ttagtaacta ctcgttggcc ccggattctg gtaactaaaa gttgctggtc agtggtcagc    180
aggtgagcat attcatggca gatttaaaag catgacccct agaaagattg tcatccttat    240
ttcttacctg aattggtact cccaactcct cccccaatgc acgcatcttt gccaaaccag    300
tctggtagtt tggaccacct cttctgacat atatgtgcat ttgcgctgct ttaagctttg    360
attcctgtag agtgatgagg aaaccaactc ataaactttc aaattaacaa gttgaagcag    420
attmagaata caactaacga taacacacct tctctttcag ggctcgaata atcccgttga    480
atgtggcagc aacatc                                                    496

<210> SEQ ID NO 5
<211> LENGTH: 600
<212> TYPE: DNA
<213> ORGANISM: Glycine max

<400> SEQUENCE: 5
tggggttttt gatgctgaca gcttgagact aagatgtcgt attgcactat ccacatactt     60
ttcacctcca gcagctttaa gcgggtaagt ttctgcccaa cagatcagac ccaatttttac    120 tctctattgt attaaacatt gagcattatt ttaaggatgt agtatcgtga agtcttactt    180
ccatttggtg atccatattg tggtatacta tattgcagga atcaatctrc gtatcctgtt    240
```

| | |
|---|---|
| gccattgcgg ctcatccact ggaacccaac caatttgctg ttggattgac agatgggtcc | 300 |
| gtgaaagtga tagagcctag tgaatcagaa ggtaagtggg gaaccagtcc acctatggat | 360 |
| aatggaatat tgaacggtag ggcagcatca acatctataa caagcaacct cacacccgac | 420 |
| caggcacaaa gataagaaca ttcattgtac cataccagca tattctttcc acctgtaatt | 480 |
| tgatcacctt agattttag attttgattc cccccaattt gtccctaaac aaggtcttgt | 540 |
| cagggtcagc tcggacataa aaatggcaaa tgtaagctct tgtcttgtaa acctgaacgc | 600 |

<210> SEQ ID NO 6
<211> LENGTH: 401
<212> TYPE: DNA
<213> ORGANISM: Glycine max
<220> FEATURE:
<221> NAME/KEY: misc_feature
<222> LOCATION: (312)..(312)
<223> OTHER INFORMATION: n is a, c, g, or t

<400> SEQUENCE: 6

| | |
|---|---|
| atattttccg cttattatg ccttctttc attcaaaatg aatgatctta ttttgagttg | 60 |
| agatgatttt attaatattt gaacaagttc tattatgatt ttactatgcg aatgtgaatc | 120 |
| ttttacccctt ttgaaataaa taaaagtaca aaaaatataa aatacaattg aggtgtccat | 180 |
| acaatatctg acatgtactt wtacttgaca caattacaac acgacatgac gtgaccacta | 240 |
| tttagaagtg tccctacttc tcaatattat tctgaaaaaa aaattaggac atcttttgta | 300 |
| catccttggg cnaaagatct taccatttcc aaagtagcta gacttacatc tatttttca | 360 |
| tttcaattca agagttctca tatgtttcca ggccccttgg a | 401 |

<210> SEQ ID NO 7
<211> LENGTH: 401
<212> TYPE: DNA
<213> ORGANISM: Glycine max

<400> SEQUENCE: 7

| | |
|---|---|
| ttgttgcatt gagcgcaagg tgttcaacaa ggtttcccaa agaagaatct ctttctcgta | 60 |
| cttagatttg agcttcaata gggtttgttt cttccgctct ctcaggagcg tatccgccgg | 120 |
| ctcttggtcg ggaacggagg gcggcgaggg ggagtggatg cggcggcgct tgcgcttgaa | 180 |
| gacgaagccg tcgtcgttgc rgagctccca cgggtcgtct tccatttga cgttggattt | 240 |
| ttccttgcaa taatatgccg ctactaccct ttcccttat ttattttca ttacacacaa | 300 |
| ttgctatcaa ttctctgact ttaattagta gtaccctata aaatttaaca tcttggtttc | 360 |
| tttttgttt ttgcgctgta tagtcataag attgatttt a | 401 |

<210> SEQ ID NO 8
<211> LENGTH: 401
<212> TYPE: DNA
<213> ORGANISM: Glycine max

<400> SEQUENCE: 8

| | |
|---|---|
| acctcatata tgatatgatg ttcatgtcat ttttctcttc cgacagaagt ttcaaagaag | 60 |
| aaaaagaaga aatctaaaag caagtgagga cttggcttct tctgccatta atgcttattc | 120 |
| tcttgattgt gatgttattt tatctcaggt tctgattta ttttgcgtc atcaggaaaa | 180 |
| agaaagaact cttgcaacag rctgatccac catcaatttc tgttattgac cttttcccat | 240 |
| ctggagattt tcctgaaggt gaaattcagc agtacaaaga cgagtaagtt gatgatgaat | 300 |
| aaatttctgc aatatctgac attttccttg caaatttgat ttgaatttga atgagtaaag | 360 | tgaattctgt tcctttttttt tattctttga ttttttttgtt t                401

<210> SEQ ID NO 9
<211> LENGTH: 1174
<212> TYPE: DNA
<213> ORGANISM: Glycine max
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t

<400> SEQUENCE: 9
gccctcccat catccagcac cggcactcac aacgatctca accccctttt accaagggct    60
ttcatgtctt ctaagaaagc cgtatctttt tcatcaatgc tctgtgtttt tggagctgat   120
gacargctca ccgactctga tttcacaata gttggtccag atgtaccaga gactgcccta   180
gaggttgaca ctgccggttt tggctttgtt ttagacattg ccgcttctct tctcactcgc   240
acagatgcag gaacctagcc aaaaacaaga tatagactca attagagaat atatacaaag   300
agattgaaat aataacaagt gatgccagtt ttaagttctc aatcataaac agntcagata   360
tatgttanat taacttattt aacagctatc tttcctcatg attcaactca cagataacac   420
ttcttccgtt aagaaaatat gtcccataca agtaaatgca caataaatca tttagttgtt   480
attagtttgg tttatataat cactacatac cgtagcaaca aacaattacc accagactaa   540
attacagaat gatggcatta gcttctttcg agttcaggaa agcttataat canaacacta   600
aaaacttcgt accccattgc ccagaggctc ttcgctatgc gaaggtatgg gggagggata   660
ttgtacgcag ccttacccctt gcatatgcaa agaggctgtt tccggatttg aacccatgac   720
caacaagtca ccaaggcaca actttaccgc tgcaccaggg ctcgccctcc ttataatcaa   780
aaccctgttg aaagaaattt ttacttgaaa aactcttccg ttatagaatt aagccaaaaa   840
caaacaagta atagagatcc ctaaaagaag aaaaaattaa gagcccatat aaaaagaagt   900
gcaaaaaaaa aaaaatcctc aacttaccat ggctgttagt tctggagtgt gttgagctaa   960
tggcctttta acaacagtag aagcagcaga tttaacatat gatggtttcg gaggaggagg   1020
aggtggccta gttgctatat gatcctcttc ctggaagttt ggaggaggac caggaggaag   1080
tggaggtctc atcattggag gaggaccagg tggaggacca ggtagaggaa aaggggggtgg   1140 ccttggcatt aggggggacca tcattccagg aggt                              1174

<210> SEQ ID NO 10
<211> LENGTH: 367
<212> TYPE: DNA
<213> ORGANISM: Glycine max

<400> SEQUENCE: 10
attcattcac taattgatta ttagccttag aaattcaaat gatataatct gaccactcag    60
agataaagga agtatggtcc atggactccc caggaacatc ctcgtgctta gagggcttct   120
ccttcccacc aaccaacctg gctgggttcc aacagctgt tgtctgtggt ggcacatcga    180
ttaaaaccac sgagccagca ccaacctttg caccttcccc gatcttaata ttccccagaa   240

```
tggtagcacc ggcaccaata agcaccccat ccccaatctt gggatgccgg tccccaccaa    300
ccttgccagt cccacccagc gtaacgtggt gcaggatcga cacattgttc ccgatcactg    360
gccccgt                                                              367
```

<210> SEQ ID NO 11
<211> LENGTH: 368
<212> TYPE: DNA
<213> ORGANISM: Glycine max

<400> SEQUENCE: 11

```
attcattcac taattgatta ttagccttag aaattcaaat gatataatct gaccactcag    60
agataaagga agtatggtcc atggactccc aggaacatc ctcgtgctta gagggcttct    120
ccttcccacc aaccaacctg gctgggttcc aacagctgt tgtctgtggt ggcacatcga    180
ttaaaaccac cggagccagc accaaccttt gcaccttccc cgatcttaat attccccaga    240
atggtagcac cggcaccaat aagcacccca tccccaatct tgggatgccg gtccccacca    300
accttgccag tccacccagc gtaacgtgg tgcaggatcg acacattgtt cccgatcact    360
ggccccgt                                                             368
```

<210> SEQ ID NO 12
<211> LENGTH: 402
<212> TYPE: DNA
<213> ORGANISM: Glycine max

<400> SEQUENCE: 12

```
cgctaatagt accacctact acatcacagc tagccataat acctaaacct ctttcgtaca    60
aatattgcag caaaacaatg catagttcct gcgttgagct tccccttgta ctgttaaggt    120
caaccataat agatgaaaca caatctgctc agctggaagt atgcagaatt agagcaatca    180
atgaatagag cttcataaga atgctctagt cttggggtag aagtgcgatc tcgatttcat    240
gaagtgactt ccctttggtt tccaccacat ttcttttac aaaaattact gccatgatgc    300
aaaaggtagc aaacatagag taaagcagct gtggaccaag tttctccagc aaacgcaaga    360
acagtagtcc aacaaagaaa tttatcacct gtacaagacc at                       402
```

<210> SEQ ID NO 13
<211> LENGTH: 1093
<212> TYPE: DNA
<213> ORGANISM: Glycine max

<400> SEQUENCE: 13

```
tgaagcaggt gcactctgca accaatacaa aatacccttt aagcacttat cttgtttcta    60
tgataagaaa gacaacttta tttactgctc cttttagatt tcttttctta atttaaattg    120
ttgaaacttt cccatgtacc cctaaacatg tttgaataat caatatgatt gaatcatata    180
cataattaaa actgaatttc atgaaatttg attagaaaat aaagaacatg catcttacca    240
gaggaattcc tttgagtgct ctttcttcca aataccttga gggtttatag aagttaccat    300
ataattgtgc ccattttttt aggctggtaa atatatgatt agccccaacc aaatctgccc    360
agaaaacaat gccaccctg ccaaaaaat tgattgaaat gagacacaag ctaaaaaaca    420
gggctgacat atawagcatg caaactgttc aaaagtcaaa acacaaacgc tggaggaaac    480
tgcaagtaca tgggacacaa ggacattatc aattctactt tctgcagata ctaattacac    540
atttcatcag atcttgatta aacataaaca attattatgt tttgcaacct ggrcacaagt    600
ttagtttata aggagttcaa acagtttgca aattgttata tttaattatg taaccatgtg    660
```

```
ataactttat aatgcccttc cttagtgatt catgcacttc attgctcctt ggttgatgca    720
taataggcac aaaaagattt agcaaataat ctcgacagat tctcttttgc tttcccccaa    780
taaaattgtg ttgtgctgca tatcacttgc aattagctag tggaccagta acacctttig    840 gctttctcta acaacacatc tcattttgtt tcattttigt tgctgttcct tattggttat    900
tggtttttat ttcttattg cacactgcgc atattatttt tgaagatttt actcagcttt    960
atctccttgg tcccattct cagttatgtc aattttaaag agtgaaaaaa aggaaatcca   1020
accggtaatt tgggaagctc attccaagaa cagataagag gtcaaggtct gatgctcgta   1080
taacaactcc atc                                                     1093

<210> SEQ ID NO 14
<211> LENGTH: 500
<212> TYPE: DNA
<213> ORGANISM: Glycine max
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t

<400> SEQUENCE: 14
aacatggtgt ccatcaacgc aggcttaatg atggcgcatg atctctccat caaacaccct     60
tacctaagag gagccgctga gatgtacgag gatggggttt tcgtgaccgt ngatttrgct    120
ttcttggtgg acgcncacat ctgtgtctac gaggatgtct catcctacgg tcgttatttg    180
tgcttcaatc acatcataaa cacccatgag gacgctgttc agctcgcccg caagttgacg    240
cctggtgcat cttcctcctt gccgcaaagg ttggtcagag ggcgttttig gtcattttga    300 cttgtgtttt tctttgaatg ttgactttga ctttgacata ttcaactctt ttttttatt    360 tttttatgca gtgatgacta tgggaagagt tttatcgaac agagaattag caacaagaag    420
ttgaacaaat tgatggtgga cttcgaggca taatcgactt ccatggtcat cctttigggac    480 ggtgattaga gcaatcacat                                                500

<210> SEQ ID NO 15
<211> LENGTH: 501
<212> TYPE: DNA
<213> ORGANISM: Glycine max

<400> SEQUENCE: 15
cttgacctac gtgaaggaga aaacggtgtc gtcagagaaa acggtgagga gttcggtgga     60
ggaggatggg tcccacgggg gcatgccgtg cttcgggcag ttattcggtg cgttccgcga    120
actgaagcgt cccatgtgga tccttctgtt ggtgacgtgt ctgaactgga tcgcctggtt    180
cccttttttg ctattcgaca ccgactggat ggggcgtgag gtgtacgag ggacagtagg    240 ggaagggaag rcgtacgata ggggtgtccg tgcgggtgcg ttgggctga tgttgaactc    300 tgttgtgctt ggtgcgacgt cgttgggagt ggaagtgctg gcgcgtgggg ttggggcgt    360 caagaggctg tggggattg ttaacttctt gctcgcggtt tgtttggcca tgacggtttt    420
ggttactaag atggcccaac attctcgaca atacacccta ctccccaacg cccaccagga    480
acccctgcct cctcccgccg c                                              501

<210> SEQ ID NO 16
```

```
<211> LENGTH: 620
<212> TYPE: DNA
<213> ORGANISM: Glycine max

<400> SEQUENCE: 16
cttcccttct cttaatataa ttttgagata aatatcgctg tcattaaaaa atgtatctag      60
ctgtgtaatt ggaaaaagaa tttgtaattg actatgaatc atcctaatttt tactttgcat    120 gagctatctc accagacttg tacattcttg ctcgtcttga atattcttgg atctttcgat    180
cacgctcttt gagcatctga tccatgttgt ttgatgaaag cagtaatgga ccagagaggt    240
ggtagatatt gtttcccatg gatccatgcc catcctgaaa tagggaccag catcaataac    300
cagcaaaacc ttaagataaa taataaatgc atacaaatta cgaaaatgtg gcaaactagg    360
gacacaaaaa gcaagatttt gtcgttgttg atggctaaca aagccattca ctaacatatg    420
ctgacaatca cgaaagcaga aagacgatag aaattggaag gaaacgatac taatagrcaa    480
aactaacctg aattaatgtt tcagttgaaa attttccatt ttcgatttgc ctgggatcaa    540
ttgtctgaga atggcgtttt ttatcatgcc ttcttcttga ctctgatcca ttagttgact    600
cctgtacttg aattgtttct                                                 620

<210> SEQ ID NO 17
<211> LENGTH: 1001
<212> TYPE: DNA
<213> ORGANISM: Glycine max
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t

<400> SEQUENCE: 17
ccctgaggtg cacgcacttt tgcggtgtat gtggcattaa ggtatccaac attggtaact      60
gttcttgtga tcacttttgc ttttttgttgc cttttaagtg tacttataga tattgatggg    120
taattgacgc tggagataag gtcttcagag gagttctttg ggcaattgaa gttagtctca    180
gagattgacc ttatgatttt ctgtgaatag ccgaaataac aaaggaatct gagatagtct    240
tccacatctg tttcaaagac taagccaggg ttgagagctc tgagtggatt aatttcccca    300
actcccattt catgtgggcc ggcaatggag tttgagctgt tagtaagagg cttcctcatg    360
ttgttgtagt ttgtagctga agaatggaat aggaacaaaa cagcataagg acatgtttga    420
ttctcttttc acttttttgt ggtaaaattt gttttctaaa acaattccat actactcagc    480
tatcatccaa aatctattaa rttttaaaag ttgtttcaaa acaagngttn caaaaaccca    540
aaaatagaan cagttggaag atgttttctt caagtgttct actcaagtgg acaaactttt    600
agaaaacaga aagaaatgtg ttcaggagca aaaatttca aatgtgctca gaaggcatca    660
cacacatcct taaaagacta gataagggcg tttgtctagt acctgttgtc atcaatgctg    720
atttgatcat tgaagaactc catttttttgt gtactgactt aatgaatgct gctgcacctg    780
tcacatgtgg gnaagccata gatgtaccag attttatggc atacaaggat ggctttttcc    840
```

```
caattggaac acttcctggt tccttacttt tgggaatcac agcggccaaa atgccaactc      900
ctggagccat gacatccggc tgacaacaa attttccata atgtgaaaga aacattcagc       960
gcattgttct caagatgttt atgtgatttg agttaatgga t                         1001
```

<210> SEQ ID NO 18
<211> LENGTH: 498
<212> TYPE: DNA
<213> ORGANISM: Glycine max
<220> FEATURE:
<221> NAME/KEY: misc_feature
<222> LOCATION: (34)..(34)
<223> OTHER INFORMATION: n is a, c, g, or t

<400> SEQUENCE: 18

```
acgcttacat tccaagcaaa atatcaaggt gtanaacacc taagaatcct taagtgaccc       60
tacctaattc aatcatttgc actccaagaa aaaattcatg ggtacaagta caacacatga     120
gaatcctgaa gtgaccccag ttttgctact tctagtgttg aactgttgat caattcaatc     180
atttgcactc caagaaaaat atcaaagtgt aaaacaccta agaatcctga attgatccta     240
tctttgttaa ctgctagttg atcaattcaa tcatttacat tgcaatcaaa atcaagatgt     300
agctggatgg ataaggctag cccttgrgta gaagctacag aaaacaaata attcaagtgc     360
aaaagcatat atacacgtaa gatcacagaa accaaaatcg tcaaatttcc ttgcctcttt     420
tatcttaagg gttccaaaat tacaggaaat tgatttttca tattttttggt ttagctacca     480 gaaagcagct cacaataa                                                  498
```

<210> SEQ ID NO 19
<211> LENGTH: 314
<212> TYPE: DNA
<213> ORGANISM: Glycine max
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (120)..(121)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t

<400> SEQUENCE: 19

```
atgttactct ctctatccaa caagaaaaat gtctcaagca agaatcacgt gctngcanat       60
ngtattccct attattccat catctcctar acgatgannt ttgtagtcat gggcgcctcn     120
nacnncacaa acgccaacaa cataagcacc gccattatgc caacagggaa gaagaggaga     180
```

```
acaagcggcg gcngagagag tgatggcaac attagtggta gcactaccat caatgctgtc      240
acggaaacca aaattagaat ggacaccact ctaaagaatc gaaccatgtt ttccccagca      300
ggtcggatac cgtt                                                         314
```

<210> SEQ ID NO 20
<211> LENGTH: 492
<212> TYPE: DNA
<213> ORGANISM: Glycine max
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 20

```
atcaaggtct acaaagcaga cacatgtgac atgtaactat atacaaaata tcacgaataa      60
ctccagcagg acctaatccg acatgattgt tacatacaaa cantacaatc acttaacgaa     120
caacaaaact mtaccagaca tgatccaaaa catccttagg cacccaaaag gaatgtaagc     180
tcnaactcta acnttgaaag gtcagaagga gttataagac tcaccagagt cactagacag     240
tggagagtta cgaggagaac ccccaatacc acctacatna ctactatcaa aacctatggc     300
ttcaagccaa aaactaatcc agggtgattc agatgtgtca cctttcatga agatattgac     360
ctgcatgtta agagctcncc gcctcctggg tgtgatatgc tcttggttaa ggacattatg     420
gggctcccta tgtcccgtnc gatttntgtt cagttttcct gggcattaag ccctcctcag     480
aataaaaaaa ag                                                           492
```

<210> SEQ ID NO 21
<211> LENGTH: 573
<212> TYPE: DNA
<213> ORGANISM: Glycine max
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t

<400> SEQUENCE: 21

```
cccccccccc agacgagaag agacacgcaa ctcgataagt atcacaaaag attacagaag      60
aaaaggaaca ttctcttctc aactatatcc tatttgttgc tgttgctgag gtggttggta     120
```

```
accaggatac cccggataac tgccatacat gttgggatcc tgtccagcag caggagcata      180
cccataattt tcataacctt gtgcagcata cccatagtat ccaccaccag aaccagcacc      240
accattccac tggtttggat ctgcctgagc ctgagaaaca gagcattcaa aattcaaact      300
cattaaaaag aatcagaaac atattgaaat caagtgcaga gatgcaacac tataactacc      360
tgtttgtttg aaggactgcg rccccatgaa agacgaacat tttgaccacc aacagggtc       420 ccattcaaca cccgaagtgc ctcttcngca cagctcctgt tgcatgaaaa atcaagacac      480
agtaagagag ctgcctagac tagtgttatc acacaaggtg aatgttcaat aaggagagg       540 ttacattacc tgtctgcgaa tgtgccccccc aaa                                  573
```

```
<210> SEQ ID NO 22
<211> LENGTH: 1001
<212> TYPE: DNA
<213> ORGANISM: Glycine max
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (986)..(987)
<223> OTHER INFORMATION: n is a, c, g, or t

<400> SEQUENCE: 22
```

```
ttaattaatg caaacattat atttagaatt tnaaaaaaaa acacacatta agaagtttta      60
ttcttagact catccaaata taaaacactc aatctaagtt gcaactacat atacaacatt     120
ggtcattata aacacaactt taattaatca ttctaatgac caattagcaa aaagcattaa     180
agaaaaaaaa taatttaatc tcatggtcat aagacttgca ttgaataaaa gaggatgcaa     240
ttncaagtga ttcccatgaa gtttatctat ccctaacata agagaatcta acaatacaaa     300
ataagatgat aatggatcna attgattgca atagaaacaa tagaaaataa gatgatataa     360
tggatcaaag tgattgtaat aatcaaggat cttctctcgg aggcttgagt cgtcaataaa     420
tttnttggga aactaggttt ttcatgcatg agatatact cctctgctgg accgtaacat      480
tagcttttat agtgcctcaa wagtttgctc cccattgttt ggtgcaacgc ctcaaatttt     540
ccttgttggt gtttaacgtt caggctcaac gtttgaagcc ccacatgacc ttaaataaga    600
attatgatga tgatttgtgt tttaattaga gctagccaaa nattccaaac actattaaaa    660
cttagaagag gtgcnttcaa gggtgtcaat gttgattcta gtaattcccc attccggagc    720
acttcaagcg ttgacatgtc acacgcctac gacattacaa cattttttcct atcatttcta    780
```

```
ccatttttaca acttttagct gagactttca aaattggggt gtctactata actgcagcat    840
tgaaccttgc tttggcgttt taaacatatt gaggccaatt tcttcaattt ttactttttcc   900 tacataaaat aaaaatatat atctaatttt aaaaaattat gtgccaattt cgccatattt    960
taatttttcc tttggcctcg ttctcnncta cttttgagtc t                       1001
```

<210> SEQ ID NO 23
<211> LENGTH: 654
<212> TYPE: DNA
<213> ORGANISM: Glycine max

<400> SEQUENCE: 23

```
gagtgataga taaaccagtg aaatatattt atttatcata aacagaaaaa gaaaaacaca    60
atatgtagga cgcaatgacg catgcaggcc atgtttggct tatttagtta tttatggatc   120
ccgaggtaag ggaagttgta tgcatacgtc ttcaatgctg acgttcacac ctgagtagaa   180
gcagggggag cacggtaacc tgaaataaaa agtatttatt atagaagtca tatatatata   240
tataggagaa gataaaaaga tgaaaaatat ttttcttgaa ttccttaact aacaccctaa   300
tcacactagc atttttgaag aaaagagaga cctccgcagg tggttccggg aggaacatct   360
tttccacact gcctgagggt atagacaact tttcccccgc tgaagtatga ctgaaaattg   420
ttagcaagtc ggcacatgca gggcacatca acatttctca gagcgttgca gcattctgta   480
gatggcggaa tagttggccc tccgggttta tagtactcct cgcattcctc ttgaatagta   540
cccaaattac cattgcatac ttgagccgag atgcgtggca ctgctacaat gccagcaacc   600
accaacatta ttgtaaacmc taatttaatt ccctgcatcc tcaccctccc tcta         654
```

<210> SEQ ID NO 24
<211> LENGTH: 276
<212> TYPE: DNA
<213> ORGANISM: Glycine max
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t

<400> SEQUENCE: 24

```
cgccgaggta tgtggaaaag gcccctaagt ttgtgaagcc caaggtgagc ccacgggcta    60
ttcaccagcc caggtagacg ccacccggcc cattccccca ncaccaccag ctatgtacat   120
aaaaaaaaan aagtgtcaag cgcaatgact tcgtctttag agctttcttt acattttcca   180
gattttwatt ttcgtgttga tcttcttgtt actctgatgt tccataaaga taaactcaag   240
tttctttgat gatgatattt gcgacgcctg taagtt                             276
```

<210> SEQ ID NO 25
<211> LENGTH: 1116
<212> TYPE: DNA
<213> ORGANISM: Glycine max
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t

<400> SEQUENCE: 25

```
caatatttgg ggaagaacgc tatggggaac ctttatcaga agatcagatt accctgcctg      60
ccattaagta ttctttaatt aaaagaagca atttaagatg ggaaacagaa gtgcgctggg     120
attgtcctca aaagttacca gaacaatggg gtatattatc gtgaaagcaa gataggtcca     180
ttctccgcag cagtttgaga attgccataa ttattactgt tatgccttgt catctggatg     240
tcacgtgaaa attgagtcct tgctttcgca tatggagctg cccttgctac aaatgaaaat     300
caatagtata aattttttcat tcaagataat cttcatttnt caatgcttag caaatttaac     360
tgtnggccat tcaccatttt tacnaattca acccaagttt gaagtgacaa gttccctcaa     420
attcaaattt cttttatcct gggaaactac tgttggaaaa catgraggct gtatagagag     480
agcaagggaa aaactcggaa tgcaagtatg caaggtggac cataaataac gcactacatt     540
actaacggtt ttaccaagga caatggttaa aaatcaaaag tgatttattt ttaattaant     600
gtganatatt actaatnttt ttttaccatg ttttctagaa gaagaaaaaa aaatatttat     660
tatttttttt atccattgcc tttagggcgg caaagatcag caaaacacat tagtatatta     720
ataattctcc tantcataaa aaaaatatna ctaattttcc taatgattcc acataaatgt     780
gtgtatttca aattctcaaa ataattgcta ctcaatgcga gcttatgttc agaagacttc     840
acaacataaa anaaatgccg gccttgtgcc cgtttatatt aatgttttta acataacgct     900
ggccttgtac cagcttatat taatgttttt aagtacaagt gcaatacaac tagtataaac     960
tcgacccaat gacattttac taagataact ataacccaca aattaacatt cttacctgta    1020
atttgctgaa cacagaggat attctgtcgc cttttccacc agcaaactga accaaaggga    1080
gaagtagaag agtaaaagaa gcacctaacc caatac                              1116
```

<210> SEQ ID NO 26
<211> LENGTH: 560
<212> TYPE: DNA
<213> ORGANISM: Glycine max
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (412)..(412)

<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t

<400> SEQUENCE: 26

```
tgttcgcgtc acgaagatga tcgaggtggt gttgaacgat cgattgggga agaaggtgcg      60
cgtgaagtgc aacgacgatg acaccatcgg cgacctgaag aagctggtgg cggctcagac     120
gggcacaaga gccgacaaga tccgcatcca gaagtggtac accatataca aggatcacat     180
cactctcaag gattacgaga tccacgacgg catgggtctc gaactctact acaactaaac     240
acaaggtcta tacccatctc aattcttctt tttatagata ctagctaggg ttttgttttt     300
tagggttccc raattttgat tgttttttcg gcaataatca atggtttgta acgattatgc     360
ttcttttaat tcttcgagtt agacaataat agcgtnaaat tttcgttttt tnttgtttca     420
ggtgtgtttt atgcatgata tattactatg atctgggaat gggatgaggc gccaaatgta     480
attttgactt gcgaaagtcc ctatgatttg aataatgtnc atcccgaat gatattgggt      540
attacatacc gatgacaccc                                                 560
```

<210> SEQ ID NO 27
<211> LENGTH: 961
<212> TYPE: DNA
<213> ORGANISM: Glycine max
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t

<400> SEQUENCE: 27

```
ggagagnatg gttgaaaaga atgaggaatc taatgatgtt actacagacc ttgagttgaa      60
gactcctggg tcttctgcag atcaggttag tgttgttttc caaggatatc ccatgataga    120
agatgcatcg gattcaagtt gtgtgtgtgt gtctggtttg caggatttat catctggaca    180
aagaaaatct agcaagttgt caaggaggga aagcagctgc actgaatgga gttcattagg    240
taggtgttct tcttgtagcg ttcaggacag ctcatcaagc agtgtggtgg cragcagaaa    300
ggataangaa tgaaaagta gacaagttag tcaagttctt gtgccttgaa gctgctgaag     360
tttttcattg tgcatctgct gcaactctgg aggtataagt cattctgttc taatcccaaa    420
ataaaagtca cttctgttat ctcttcttga ctaagaattt ggtccaagta ggtttaagtg    480
ctacataatt ttagcataaa cttcccttc tggggaaaa cttgaaattt cagctgcaaa     540
atgaccaagt tgaccagtgt ggcttacgtg taggtttgta aattctttca tagttgttat    600
aattgcatga ttcgatacaa ttcagcaagc taacgatttg tatcatgcaa tgaattgtcg    660
atgactttga tctgtacaat acttgcatga attgatgata tcaatgcaat ttcatatagt    720
tagttcaaat cactcaagtc tgaaactcat tatttgtgtt gctaatttc atcaaagaaa     780
ttggaaagcc aaaatatact tggattgtta aatgaaaagg aactgaagta gcactagtga    840
cgcacttact tgattattcc attgttttct tccttgtgaa accagggct taacagattt     900
tactcactct gtactttatt taactatttc attgctctat ttttatttac ttgtagaatc    960
g                                                                    961
```

<210> SEQ ID NO 28
<211> LENGTH: 401
<212> TYPE: DNA
<213> ORGANISM: Glycine max
<220> FEATURE:
<221> NAME/KEY: misc_feature
<222> LOCATION: (80)..(80)
<223> OTHER INFORMATION: n is a, c, g, or t

<400> SEQUENCE: 28

```
atacaggagc gaagtggagt ataccatgca gaatccggtt caaggccgtc gtcacattta      60
ggtggatagg tatctctaan cagcttatta taacaattgt tgtcttgaga cttctgccat     120
acagcaatgt caccctttgt attgaacatt ttaaagcaca atgaagtcag caattcctgc     180
aacttctcat aatctgatct rtttgcatca atggttgtgt tccatccacg ccacctgcgc     240
ttgtagttga tcggtggacc agacaagacc caaaatcctc caggacgaag tatccggtga     300
atttcaagga gataaattcc acctaaaata agatacctcg tcaaaaagaa tgagaattta     360
gagtgaactt ctcagctcta agcataaaga gattagcaga a                         401
```

<210> SEQ ID NO 29
<211> LENGTH: 501
<212> TYPE: DNA
<213> ORGANISM: Glycine max
<220> FEATURE:
<221> NAME/KEY: misc_feature
<222> LOCATION: (294)..(294)
<223> OTHER INFORMATION: n is a, c, g, or t

<400> SEQUENCE: 29

```
ggcgaagagg ccaagcacat gcgaacgccg aagcagagaa acagcacggt ggagacggcg      60
acgcgcgtaa aaaccttgag gggaaggggc tggttccgga agcgcgtggc ggtcggaagc     120
gaaggctggg ggtggcgaca gagtccggtg accggataat gcaactgcgg cattgaatcg     180
cggtaggggt ttggtgggga taatgagaaa tgaatgataa taagggtttg ggaaaagata     240
agggtaacgc rgtgagtgta gaccgagagg gtaatgcgtt tgtagcaaca tggncattgt     300
tgagagactc aaggccaaca acctctacaa accatttctt cgatcaaaat gctcagtccc     360
cattagttat cactttgact gctttttttc aatccggtct ccacccttta tttatttatt     420
ttttaaaaaa atactaagtt ggtgtttaca attgtataaa ctttttatcc atagaaagat     480
ttttttcttc tccatacccac                                                 501
```

<210> SEQ ID NO 30
<211> LENGTH: 401
<212> TYPE: DNA
<213> ORGANISM: Glycine max

<400> SEQUENCE: 30

```
ttcttggaaa ccttgaacag tttgctcatc ctgaaccgtg ggtagagccg ccgccgccgg      60
cggcgaagag gccaagcaca tgcgaacgcc gaagcagaga acagcacgg tggagacggc     120
gacgcgcgta aaaccttga ggggaagggg ctggttccgg aagcgcgtgg cggtcggaag     180
cgaaggctgg ggtggcgac rgagtccggt gaccggataa tgcaactgcg gcattgaatc     240
gcggtagggg tttggtgggg ataatgagaa atgaatgata taagggttt gggaaaagat     300
aagggtaacg cggtgagtgt agaccgagag ggtaatgcgt ttgtagcaac atggccattg     360
ttgagagact caaggccaac aacctctaca aaccatttct t                         401
```

<210> SEQ ID NO 31

```
<211> LENGTH: 401
<212> TYPE: DNA
<213> ORGANISM: Glycine max

<400> SEQUENCE: 31
ccccattgaa gatagcgatg atctttggaa ttaaacccca aagttaaatc ttgatatttt        60 tttcttttc ttttataggg attggccact cttagaaggg tgaatattaa catggaatga       120
agaaaggtgt ccattagcat aaagaaaaag gaaaaaaga aaccttagtg ccattatcaa       180
tttcccacct ttccttgcct wgtcatgttt taggctttcg aaagagacga agaacaattg       240
agtatcatca cgaataaatg ccacacaccg acaatacatg cattttcct ccatacacat        300 tataattcca attctgaaaa agaaaagcac taaaacaaaa acaaaatacc atatacgaag      360
gttttgccga agagccagca ctcagcacag ctagccagtt t                          401

<210> SEQ ID NO 32
<211> LENGTH: 492
<212> TYPE: DNA
<213> ORGANISM: Glycine max
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t

<400> SEQUENCE: 32
aaattccaaa ccagttcaat ccttttcagt catctctttg gtcacgtttt cacagtaaca        60
taacatattc tgtggaaata tggcaaaact tggagactgt gcagctcatt tttttattgc       120
agcaatggtt ttgagcacgt tttacgtgac caaaactgtg gcacaatcag anattgcacc       180
cacatcgcaa atggagactg gtgcagggtt tgctttgtct gtttctgggg tgaccttatg       240
ttcttctgtg ttggtttcta ttgtggcatt tatgatgcag tgaattgcaa ggcatattgg       300
ctcctattca tgtttgattg gtcttatcat gtacgtgntg aaattatatt ttatgatgaa       360
tttaaagggt tgttttgtt tctttactat gcttgcttct tgaacacggt cctgtcgttt       420
ttggcattgt aacmtagtac tagctttatg atgagttaca tgtttgtaat tttcgccaag       480
tacttaactg gt                                                         492

<210> SEQ ID NO 33
<211> LENGTH: 748
<212> TYPE: DNA
<213> ORGANISM: Glycine max
<220> FEATURE:
<221> NAME/KEY: misc_feature
<222> LOCATION: (655)..(655)
<223> OTHER INFORMATION: n is a, c, g, or t

<400> SEQUENCE: 33
aaccttctcg ggctttggtt ggttggtgaa gaaagtgtac ccaaagcaac atcaacattc        60
tagacccttc cttttcattc tagaccattc cacacacact caacacatat aataataatc       120
atcatagttc ataaccctca ccccaatcca attattatta atcactaagg aactcggaaa       180
aaagagggca ttggcattgc aaatggctcg ttacggcgag ggcgacaagc ggtggatcgt       240
ggaggaccgc cccgacggca ccaacgtcca caactggcac tggtccgaga ccaactgcct       300
cgactggtcc aaaaccttct tcagcaacct cctctccaac ctcccatcc tccacggcga       360 ggctaacctc ttcctcaaaa cgacgtcgct ccgctccctc gacggcgagg cctacgtcaa       420
```

```
cgtccgcaag gggaaaatca tccccggcta cgagatcagc ctcacactca attggcaggg    480
cgaagccaaa gattcccagg gaacctcgct tcttaaagtc gacggcaccg tcgagattcc    540
ctacatctcc gacgagaacg ccgacgarga tcccgaggtt agggttaccg ttaacgatga    600
gggaccggtt gggatgagga ttaaggacgc catgctttcc aaggggaagc ccttnatctt    660
ggagaaggtt agggtttggg tccagagcat ggccaaaggt ggtcctgtta aggatgaatt    720
ggaacccaag aaggttgcgc cgtcgttg                                      748
```

<210> SEQ ID NO 34
<211> LENGTH: 244
<212> TYPE: DNA
<213> ORGANISM: Glycine max
<220> FEATURE:
<221> NAME/KEY: misc_feature
<222> LOCATION: (55)..(55)
<223> OTHER INFORMATION: n is a, c, g, or t

<400> SEQUENCE: 34

```
aatttactta cgtgggtgca taaattattt ttccattata agaaccgggc agccngccat     60
ttccttgcgg aagaggaggg rgataccata atattatgcg taccattgaa agacatgtgt    120
ggttctcaat cagtggattt ctcttttacg gaatatgtta tgagcttttg tagaatgagg    180 agttttttgac ccaacagatt ccatacatgg tattttgaga ttgggcaatc atggttgtta    240
tgtg                                                                 244
```

<210> SEQ ID NO 35
<211> LENGTH: 401
<212> TYPE: DNA
<213> ORGANISM: Glycine max
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t

<400> SEQUENCE: 35

```
gagcgaatgc aaatattaat cgggaattac cagttgggca ggccatggag gatcgggtaa     60
cgaatcaaga accaaggaga aatggtgata ccacctttac cccttactct taccgtagcc    120
caaccttgga agccatggaa atgggacaga agtaatagtc ttctatagca ctaatcttct    180
ccctagctac ctagttcctt wcttttgtgt atacttatga gcttctctac acggcaacca    240
ctagatttag ctaattgtgc agcttctgtt tcttcntgca ttattattat tattggcact    300
gccactgtaa aaaatgaaaa atgncggctt ctttccgctg aattagatta tgttnataga    360
tggtacgtta atgggatccc attttgacct tataatgggg a                        401
```

<210> SEQ ID NO 36
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 36
tgtttgccag gacctataga ca                                           22

<210> SEQ ID NO 37
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 37
gctgctcgtg ccatgttt                                                18

<210> SEQ ID NO 38
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 38
ttttctccag atgttaga                                                18

<210> SEQ ID NO 39
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 39
ttctccagat gttgga                                                  16

<210> SEQ ID NO 40
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 40
tgttgctccg accatgttct                                              20

<210> SEQ ID NO 41
<211> LENGTH: 23
<212> TYPE: DNA
<213> ORGANISM: Artificial Sequence
<220> FEATURE:
<223> OTHER INFORMATION: Primer and Probe Sequences

<400> SEQUENCE: 41
gaaagccgct gtatgaatct gaa                                          23

<210> SEQ ID NO 42
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 42
ttcttacttg actcatata                                               19

<210> SEQ ID NO 43
<211> LENGTH: 19
<212> TYPE: DNA
<213> ORGANISM: Artificial Sequence

```
<220> FEATURE:
<223> OTHER INFORMATION: Primer and Probe Sequences

<400> SEQUENCE: 43
ttcttacttg actcttata                                          19

<210> SEQ ID NO 44
<211> LENGTH: 23
<212> TYPE: DNA
<213> ORGANISM: Artificial Sequence
<220> FEATURE:
<223> OTHER INFORMATION: Primer and Probe Sequences

<400> SEQUENCE: 44
gtcaagctct tcaaaaccac caa                                     23

<210> SEQ ID NO 45
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 45
ggccagaagc aaatgcgaat                                         20

<210> SEQ ID NO 46
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 46
tgcgccaatg aattc                                              15

<210> SEQ ID NO 47
<211> LENGTH: 13
<212> TYPE: DNA
<213> ORGANISM: Artificial Sequence
<220> FEATURE:
<223> OTHER INFORMATION: Primer and Probe Sequences

<400> SEQUENCE: 47
tgcgccaatg cat                                                13

<210> SEQ ID NO 48
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 48
ttcgagccct gaaagagaag gt                                      22

<210> SEQ ID NO 49
<211> LENGTH: 23
<212> TYPE: DNA
<213> ORGANISM: Artificial Sequence
<220> FEATURE:
<223> OTHER INFORMATION: Primer and Probe Sequences

<400> SEQUENCE: 49
tgcgctgctt taagctttga ttc                                     23
```

<210> SEQ ID NO 50
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 50
tcgttagttg tattctgaa                                           19

<210> SEQ ID NO 51
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 51
cgttagttgt attcttaatc                                          20

<210> SEQ ID NO 52
<211> LENGTH: 24
<212> TYPE: DNA
<213> ORGANISM: Artificial Sequence
<220> FEATURE:
<223> OTHER INFORMATION: Primer and Probe Sequences

<400> SEQUENCE: 52
gtcttacttc catttggtga tcca                                     24

<210> SEQ ID NO 53
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 53
tcacggaccc atctgtcaat c                                        21

<210> SEQ ID NO 54
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 54
tgcaggaatc aatctacg                                            18

<210> SEQ ID NO 55
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 55
caggaatcaa tctgcgtat                                           19

<210> SEQ ID NO 56
<211> LENGTH: 26
<212> TYPE: DNA
<213> ORGANISM: Artificial Sequence
<220> FEATURE:
<223> OTHER INFORMATION: Primer and Probe Sequences

```
<400> SEQUENCE: 56
tgcgaatgtg aatcttttac cctttt                                          26

<210> SEQ ID NO 57
<211> LENGTH: 25
<212> TYPE: DNA
<213> ORGANISM: Artificial Sequence
<220> FEATURE:
<223> OTHER INFORMATION: Primer and Probe Sequences

<400> SEQUENCE: 57
cgtcatgtcg tgttgtaatt gtgtc                                           25

<210> SEQ ID NO 58
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 58
tatctgacat gtacttatac                                                 20

<210> SEQ ID NO 59
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 59
tctgacatgt acttttac                                                   18

<210> SEQ ID NO 60
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 60
attgcaagga aaaatccaac gtcaaaatgg aagacgaccc gtgggagctc                50

<210> SEQ ID NO 61
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 61
tctgatttta tttttgcgtc atcaggaaaa agaaagaact cttgcaacag                50

<210> SEQ ID NO 62
<211> LENGTH: 24
<212> TYPE: DNA
<213> ORGANISM: Artificial Sequence
<220> FEATURE:
<223> OTHER INFORMATION: Primer and Probe Sequences

<400> SEQUENCE: 62
ggtacatctg gaccaactat tgtg                                            24

<210> SEQ ID NO 63
```

```
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 63
accaagggct ttcatgtctt c                                              21

<210> SEQ ID NO 64
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 64
agtcggtgag cctgt                                                     15

<210> SEQ ID NO 65
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 65
agtcggtgag cttgtc                                                    16

<210> SEQ ID NO 66
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 66
tggctgggtt cccaacag                                                  18

<210> SEQ ID NO 67
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 67
gggaaggtgc aaaggttggt                                                20

<210> SEQ ID NO 68
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 68
ctggctccgt ggttt                                                     15

<210> SEQ ID NO 69
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 69
```

```
ctggctcggt ggttt                                                         15

<210> SEQ ID NO 70
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 70
gttgtctgtg gtggcacatc                                                    20

<210> SEQ ID NO 71
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 71
tgccggtgct accattctg                                                     19

<210> SEQ ID NO 72
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 72
taaaaccacc gagcc                                                         15

<210> SEQ ID NO 73
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 73
ttaaaaccac ggagcc                                                        16

<210> SEQ ID NO 74
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 74
gctggaagta tgcagaatta gagcaatcaa tgaatagagc ttcataagaa                   50

<210> SEQ ID NO 75
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 75
gctggaagta tgcagaatta gagcaatcaa tgaatagagc ttcataagat                   50

<210> SEQ ID NO 76
<211> LENGTH: 50
<212> TYPE: DNA
```

```
<213> ORGANISM: Artificial Sequence
<220> FEATURE:
<223> OTHER INFORMATION: Primer and Probe Sequences

<400> SEQUENCE: 76
gcagtttcct ccagcgtttg tgttttgact tttgaacagt ttgcatgctt        50

<210> SEQ ID NO 77
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 77
gcagtttcct ccagcgtttg tgttttgact tttgaacagt ttgcatgcta        50

<210> SEQ ID NO 78
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 78
gagacatcct cgtagacaca ga                                      22

<210> SEQ ID NO 79
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 79
gcgcatgatc tctccatcaa a                                       21

<210> SEQ ID NO 80
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 80
caccaagaaa gccaaatc                                           18

<210> SEQ ID NO 81
<211> LENGTH: 17
<212> TYPE: DNA
<213> ORGANISM: Artificial Sequence
<220> FEATURE:
<223> OTHER INFORMATION: Primer and Probe Sequences

<400> SEQUENCE: 81
tccaccaaga aagctaa                                            17

<210> SEQ ID NO 82
<211> LENGTH: 24
<212> TYPE: DNA
<213> ORGANISM: Artificial Sequence
<220> FEATURE:
<223> OTHER INFORMATION: Primer and Probe Sequences

<400> SEQUENCE: 82
ccaagcacaa cagagttcaa catc                                    24
```

<210> SEQ ID NO 83
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 83
gaggtgtacg gagggacagt                                               20

<210> SEQ ID NO 84
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 84
cctatcgtac gcctt                                                    15

<210> SEQ ID NO 85
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 85
cctatcgtac gtcttc                                                   16

<210> SEQ ID NO 86
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 86
cccaggcaaa tcgaaaatgg a                                             21

<210> SEQ ID NO 87
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 87
gctgacaatc acgaaagcag a                                             21

<210> SEQ ID NO 88
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 88
caggttagtt ttgcctat                                                 18

<210> SEQ ID NO 89
<211> LENGTH: 19
<212> TYPE: DNA
<213> ORGANISM: Artificial Sequence
<220> FEATURE:

<223> OTHER INFORMATION: Primer and Probe Sequences

<400> SEQUENCE: 89
ttcaggttag ttttgtcta                                          19

<210> SEQ ID NO 90
<211> LENGTH: 26
<212> TYPE: DNA
<213> ORGANISM: Artificial Sequence
<220> FEATURE:
<223> OTHER INFORMATION: Primer and Probe Sequences

<400> SEQUENCE: 90
aaggacatgt ttgattctct tttcac                                  26

<210> SEQ ID NO 91
<211> LENGTH: 24
<212> TYPE: DNA
<213> ORGANISM: Artificial Sequence
<220> FEATURE:
<223> OTHER INFORMATION: Primer and Probe Sequences

<400> SEQUENCE: 91
tgtccacttg agtagaacac ttga                                    24

<210> SEQ ID NO 92
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 92
atcatccaaa atctattaaa tt                                      22

<210> SEQ ID NO 93
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 93
catccaaaat ctattaagtt t                                       21

<210> SEQ ID NO 94
<211> LENGTH: 24
<212> TYPE: DNA
<213> ORGANISM: Artificial Sequence
<220> FEATURE:
<223> OTHER INFORMATION: Primer and Probe Sequences

<400> SEQUENCE: 94
ttggtttctg tgatcttacg tgta                                    24

<210> SEQ ID NO 95
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 95
gatgtagctg gatggataag gc                                      22

```
<210> SEQ ID NO 96
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 96
ctgtagcttc tactcaag                                                 18

<210> SEQ ID NO 97
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 97
tgtagcttct acccaa                                                   16

<210> SEQ ID NO 98
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 98
tgtctcaagc aagaatcac                                                19

<210> SEQ ID NO 99
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 99
aggcgcccat gactac                                                   16

<210> SEQ ID NO 100
<211> LENGTH: 17
<212> TYPE: DNA
<213> ORGANISM: Artificial Sequence
<220> FEATURE:
<223> OTHER INFORMATION: Primer and Probe Sequences

<400> SEQUENCE: 100
catcatctcc taaacga                                                  17

<210> SEQ ID NO 101
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 101
catcatctcc tagacg                                                   16

<210> SEQ ID NO 102
<211> LENGTH: 23
<212> TYPE: DNA
<213> ORGANISM: Artificial Sequence
<220> FEATURE:
<223> OTHER INFORMATION: Primer and Probe Sequences
```

<400> SEQUENCE: 102
gggtgcctaa ggatgttttg gat					23

<210> SEQ ID NO 103
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 103
gcaggaccta atccgacatg at					22

<210> SEQ ID NO 104
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 104
catgtctggt atagtttt						18

<210> SEQ ID NO 105
<211> LENGTH: 17
<212> TYPE: DNA
<213> ORGANISM: Artificial Sequence
<220> FEATURE:
<223> OTHER INFORMATION: Primer and Probe Sequences

<400> SEQUENCE: 105
atgtctggta gagtttt						17

<210> SEQ ID NO 106
<211> LENGTH: 23
<212> TYPE: DNA
<213> ORGANISM: Artificial Sequence
<220> FEATURE:
<223> OTHER INFORMATION: Primer and Probe Sequences

<400> SEQUENCE: 106
gggtggtcaa aatgttcgtc ttt					23

<210> SEQ ID NO 107
<211> LENGTH: 26
<212> TYPE: DNA
<213> ORGANISM: Artificial Sequence
<220> FEATURE:
<223> OTHER INFORMATION: Primer and Probe Sequences

<400> SEQUENCE: 107
gcagagatgc aacactataa ctacct					26

<210> SEQ ID NO 108
<211> LENGTH: 14
<212> TYPE: DNA
<213> ORGANISM: Artificial Sequence
<220> FEATURE:
<223> OTHER INFORMATION: Primer and Probe Sequences

<400> SEQUENCE: 108
actgcgaccc catg							14

<210> SEQ ID NO 109
<211> LENGTH: 14

<212> TYPE: DNA
<213> ORGANISM: Artificial Sequence
<220> FEATURE:
<223> OTHER INFORMATION: Primer and Probe Sequences

<400> SEQUENCE: 109
actgcggccc catg                                                        14

<210> SEQ ID NO 110
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 110
ctgctggacc gtaacattag c                                                21

<210> SEQ ID NO 111
<211> LENGTH: 18
<212> TYPE: DNA
<213> ORGANISM: Artificial Sequence
<220> FEATURE:
<223> OTHER INFORMATION: Primer and Probe Sequences

<400> SEQUENCE: 111
tgaggcgttg caccaaac                                                    18

<210> SEQ ID NO 112
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 112
atagtgcctc aaaagt                                                      16

<210> SEQ ID NO 113
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 113
agtgcctcaa tagtt                                                       15

<210> SEQ ID NO 114
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 114
agggtgagga tgcagggaat ta                                               22

<210> SEQ ID NO 115
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 115
cgtggcactg ctacaatgc                                                    19

<210> SEQ ID NO 116
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 116
aacattattg taaacactaa tt                                                22

<210> SEQ ID NO 117
<211> LENGTH: 23
<212> TYPE: DNA
<213> ORGANISM: Artificial Sequence
<220> FEATURE:
<223> OTHER INFORMATION: Primer and Probe Sequences

<400> SEQUENCE: 117
caacattatt gtaaacccta att                                               23

<210> SEQ ID NO 118
<211> LENGTH: 21
<212> TYPE: DNA
<213> ORGANISM: Artificial Sequence
<220> FEATURE:
<223> OTHER INFORMATION: Primer and Probe Sequences

<400> SEQUENCE: 118
caagcgcaat gacttcgtct t                                                 21

<210> SEQ ID NO 119
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 119
ggcgtcgcaa atatcatcat ca                                                22

<210> SEQ ID NO 120
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 120
acattttcca gattttaatt                                                   20

<210> SEQ ID NO 121
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 121
tacattttcc agatttttat                                                   20

<210> SEQ ID NO 122
<211> LENGTH: 23
<212> TYPE: DNA
<213> ORGANISM: Artificial Sequence

```
<220> FEATURE:
<223> OTHER INFORMATION: Primer and Probe Sequences

<400> SEQUENCE: 122
gtccaccttg catacttgca ttc                                              23

<210> SEQ ID NO 123
<211> LENGTH: 23
<212> TYPE: DNA
<213> ORGANISM: Artificial Sequence
<220> FEATURE:
<223> OTHER INFORMATION: Primer and Probe Sequences

<400> SEQUENCE: 123
tcctgggaaa ctactgttgg aaa                                              23

<210> SEQ ID NO 124
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 124
tatacagcct ccatgt                                                      16

<210> SEQ ID NO 125
<211> LENGTH: 17
<212> TYPE: DNA
<213> ORGANISM: Artificial Sequence
<220> FEATURE:
<223> OTHER INFORMATION: Primer and Probe Sequences

<400> SEQUENCE: 125
tctatacagc cttcatg                                                     17

<210> SEQ ID NO 126
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 126
acccatctca attcttcttt                                                  20

<210> SEQ ID NO 127
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 127
agaagcataa tcgttacaaa cc                                               22

<210> SEQ ID NO 128
<211> LENGTH: 17
<212> TYPE: DNA
<213> ORGANISM: Artificial Sequence
<220> FEATURE:
<223> OTHER INFORMATION: Primer and Probe Sequences

<400> SEQUENCE: 128
tttagggttc ccaaatt                                                     17
```

```
<210> SEQ ID NO 129
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 129
tttagggttc ccgaat                                                       16

<210> SEQ ID NO 130
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 130
agcgttcagg acagctcatc                                                   20

<210> SEQ ID NO 131
<211> LENGTH: 20
<212> TYPE: DNA
<213> ORGANISM: Artificial Sequence
<220> FEATURE:
<223> OTHER INFORMATION: Primer and Probe Sequences

<400> SEQUENCE: 131
cagcagcttc aaggcacaag                                                   20

<210> SEQ ID NO 132
<211> LENGTH: 14
<212> TYPE: DNA
<213> ORGANISM: Artificial Sequence
<220> FEATURE:
<223> OTHER INFORMATION: Primer and Probe Sequences

<400> SEQUENCE: 132
tgtggtggca agca                                                         14

<210> SEQ ID NO 133
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 133
agtgtggtgg cgagc                                                        15

<210> SEQ ID NO 134
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 134
atcaactaca agcgcaggtg gcgtggatgg aacacaacca ttgatgcaaa                  50

<210> SEQ ID NO 135
<211> LENGTH: 50
<212> TYPE: DNA
<213> ORGANISM: Artificial Sequence
<220> FEATURE:
<223> OTHER INFORMATION: Primer and Probe Sequences
```

```
<400> SEQUENCE: 135
taatgagaaa tgaatgataa taagggtttg ggaaaagata agggtaacgc            50

<210> SEQ ID NO 136
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 136
acccctaccg cgattcaatg ccgcagttgc attatccggt caccggactc            50

<210> SEQ ID NO 137
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 137
tgatgatact caattgttct tcgtctcttt cgaaagccta aaacatgact            50

<210> SEQ ID NO 138
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 138
tgatgatact caattgttct tcgtctcttt cgaaagccta aaacatgaca            50

<210> SEQ ID NO 139
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 139
acacggtcct gtcgtt                                                 16

<210> SEQ ID NO 140
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 140
aacatgtaac tcatcataaa gc                                          22

<210> SEQ ID NO 141
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 141
tttggcattg taacatagt                                              19

<210> SEQ ID NO 142
```

```
<211> LENGTH: 17
<212> TYPE: DNA
<213> ORGANISM: Artificial Sequence
<220> FEATURE:
<223> OTHER INFORMATION: Primer and Probe Sequences

<400> SEQUENCE: 142
tggcattgta acctagt                                                        17

<210> SEQ ID NO 143
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 143
caccgtcgag attccctaca tc                                                  22

<210> SEQ ID NO 144
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 144
ggtccctcat cgttaacggt aa                                                  22

<210> SEQ ID NO 145
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 145
cgacgaagat cccga                                                          15

<210> SEQ ID NO 146
<211> LENGTH: 15
<212> TYPE: DNA
<213> ORGANISM: Artificial Sequence
<220> FEATURE:
<223> OTHER INFORMATION: Primer and Probe Sequences

<400> SEQUENCE: 146
cgacgaggat cccga                                                          15

<210> SEQ ID NO 147
<211> LENGTH: 22
<212> TYPE: DNA
<213> ORGANISM: Artificial Sequence
<220> FEATURE:
<223> OTHER INFORMATION: Primer and Probe Sequences

<400> SEQUENCE: 147
tccactgatt gagaaccaca ca                                                  22

<210> SEQ ID NO 148
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 148
```

```
gccatttcct tgcggaaga                                                19
```

<210> SEQ ID NO 149
<211> LENGTH: 16
<212> TYPE: DNA
<213> ORGANISM: Artificial Sequence
<220> FEATURE:
<223> OTHER INFORMATION: Primer and Probe Sequences

<400> SEQUENCE: 149

```
attatggtat cccccct                                                  16
```

<210> SEQ ID NO 150
<211> LENGTH: 19
<212> TYPE: DNA
<213> ORGANISM: Artificial Sequence
<220> FEATURE:
<223> OTHER INFORMATION: Primer and Probe Sequences

<400> SEQUENCE: 150

```
aatattatgg tatctccct                                                19
```

<210> SEQ ID NO 151
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 151

```
gtaatagtct tctatagcac taatcttctc cctagctacc tagttcctta              50
```

<210> SEQ ID NO 152
<211> LENGTH: 50
<212> TYPE: DNA
<213> ORGANISM: Artificial Sequence
<220> FEATURE:
<223> OTHER INFORMATION: Primer and Probe Sequences

<400> SEQUENCE: 152

```
gtaatagtct tctatagcac taatcttctc cctagctacc tagttccttt              50
```